United States Patent [19]

Friesen et al.

[11] Patent Number: 5,410,054

[45] Date of Patent: Apr. 25, 1995

[54] HETEROARYL QUINOLINES AS INHIBITORS OF LEUKOTRIENE BIOSYNTHESIS

[75] Inventors: Rick Friesen, Dollard Des Ormeaux; Robert N. Young, Senneville; Yves Girard, Ile-Bizard; Marc Blouin; Daniel Dube, both of St-Lazare, all of Canada

[73] Assignee: Merck Frosst Canada, Inc., Kirkland, Canada

[21] Appl. No.: 95,131

[22] Filed: Jul. 20, 1993

[51] Int. Cl.⁶ .................. C07D 215/12; C07D 215/16; C07D 217/22; C07D 217/18

[52] U.S. Cl. .................................. 546/141; 546/142; 546/153; 546/155

[58] Field of Search ............... 546/141, 142, 153, 155; 514/307, 314

[56] References Cited

U.S. PATENT DOCUMENTS

| | | | |
|---|---|---|---|
| 3,536,809 | 10/1970 | Applezweig et al. | 424/28 |
| 3,598,123 | 8/1971 | Zaffaroni et al. | 128/268 |
| 3,630,200 | 12/1971 | Higuchi et al. | 128/260 |
| 3,686,320 | 8/1972 | Fitzmaurice et al. | 424/10 |
| 3,686,412 | 8/1972 | Fitzmaurice et al. | 424/283 |

(List continued on next page.)

FOREIGN PATENT DOCUMENTS

| | | |
|---|---|---|
| 0011067 | 5/1980 | European Pat. Off. |
| 0040696 | 12/1981 | European Pat. Off. |
| 0056172 | 7/1982 | European Pat. Off. |

(List continued on next page.)

OTHER PUBLICATIONS

Crawley, G. C., "Methoxy Tetrahydropyrans . . . ", J. Med Chem, vol. 35, pp. 2600–2609, published Jul. 10, 1992.

Scand. J. Clin. Lab. Invest., 21 (Supp 97), pp. 77, by A. Boyum, 1968.

J. of Biol. Chem., vol. 266, No. 8, pp. 5072–5079, by D. Danielle, et al., 1991.

J. Am. Chem. Soc. 1982, vol. 104, pp. 4666–4671, J. A. Haslegrave, et al.

J. Org. Chem. 1983, vol. 48, pp. 2120–2122, by D. S. Ross, et al.

Am. Rev. Resp. Dis., vol. 128, pp. 839–844, 1983, by W. M. Abraham, et al.

Chem. Pharm. Bull. 38(9) pp. 2446–2458 (1990), by A. Ashimori, et al.

Nature, vol. 313 (Jul. 1985) pp. 126–131, by B. P. Richardson, et al.

Prostaglandins, vol. 28, No. 2 (Aug. 1984) pp. 173–182, by C. S. McFarlane, et al.

Agents & Actions, vol. 22, ½ (1987), pp. 63–68, by C. S. McFarlane, et al.

Prostaglandins Leukotrienes and Medicine 13, pp. 21–25 (1984), by J. Rokach, et al.

*Primary Examiner*—C. Warren Ivy
*Assistant Examiner*—D. Margaret M. Mach
*Attorney, Agent, or Firm*—Mollie M. Yang; David L. Rose

[57] ABSTRACT

Compounds having the formula I:

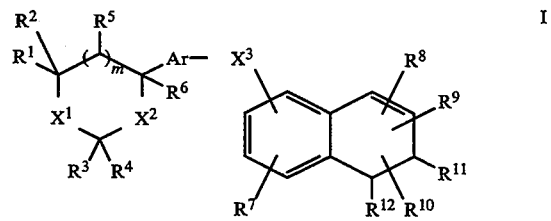

are inhibitors of leukotriene biosynthesis. These compounds are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection and in preventing the formation of atherosclerotic plaques.

11 Claims, No Drawings

U.S. PATENT DOCUMENTS

| | | | |
|---|---|---|---|
| 3,845,770 | 11/1974 | Theeuwes et al. | 128/260 |
| 3,916,899 | 11/1975 | Theeuwes et al. | 128/260 |
| 4,008,719 | 2/1977 | Theeuwes et al. | 128/270 |
| 4,237,160 | 12/1980 | Hamel et al. | 424/275 |
| 4,255,431 | 3/1981 | Junggren et al. | 424/263 |
| 4,283,408 | 8/1981 | Hirata et al. | 424/270 |
| 4,325,961 | 4/1982 | Kollonitsch et al. | 424/273 |
| 4,362,736 | 12/1982 | Hirata et al. | 424/270 |
| 4,394,508 | 7/1983 | Crenshaw et al. | 546/209 |
| 4,839,369 | 6/1989 | Youssefyeh | 514/314 |
| 5,006,534 | 4/1991 | Mohrs | 514/311 |
| 5,134,148 | 7/1992 | Crawley | 514/312 |
| 5,246,944 | 9/1993 | Greenlee | 514/312 |
| 5,260,442 | 11/1993 | Hutton | 546/157 |

FOREIGN PATENT DOCUMENTS

| | | |
|---|---|---|
| 0061800 | 10/1982 | European Pat. Off. |
| 0104885 | 4/1984 | European Pat. Off. |
| 0106565 | 4/1984 | European Pat. Off. |
| 0115394 | 8/1984 | European Pat. Off. |
| 0136893 | 4/1985 | European Pat. Off. |
| 0138481 | 4/1985 | European Pat. Off. |
| 0140684 | 5/1985 | European Pat. Off. |
| 0140709 | 5/1985 | European Pat. Off. |
| 0385662 | 9/1990 | European Pat. Off. |
| 0462812 | 12/1991 | European Pat. Off. |
| 0462830 | 12/1991 | European Pat. Off. |
| 2058785 | 4/1981 | United Kingdom. |

HETEROARYL QUINOLINES AS INHIBITORS OF LEUKOTRIENE BIOSYNTHESIS

BACKGROUND OF THE INVENTION

The leukotrienes constitute a group of locally acting hormones, produced in living systems from arachidonic acid. The major leukotrienes are Leukotriene B4 (abbreviated at LTB4), LTC4, LTD4, and LTE4. The biosynthesis of these leukotrienes begins with the action of the enzyme 5-lipoxygenase on arachidonic acid to produce the epoxide known as Leukotriene A4 (LTA4), which is converted to the other leukotrienes by subsequent enzymatic steps. Further details of the biosynthesis as well as the metabolism of the leukotrienes are to be found in the book *Leukotrienes and Lipoxygenases*, ed. J. Rokach, Elsevier, Amsterdam (1989). The actions of the leukotrienes in living systems and their contribution to various diseases states are also discussed in the book by Rokach.

Three ICI European Patent Applications (EP 385,662; 462,812; and 462,830) disclose the compounds shown below as being inhibitors of the 5-lipoxygenase enzyme. Among other differences, these compounds differ from those of the present invention in that the nature of the linking unit, $A^1$—$X^1$ or A—X, is consistently different from $X^3$ in the present compounds.

1. $Ar^1$—$A^1$—$X^1$—$Ar^2$—$\underset{R^3}{\underset{|}{C}}\overset{OR^1}{\overset{|}{R^2}}$   EP 462,812

2. Q—A—X—Ar—$\underset{R^3}{\underset{|}{C}}\overset{OR^1}{\overset{|}{R^2}}$   EP 385,662

3. $Ar^1$—$A^1$—$X^1$—$Ar^2$—$\underset{R^3}{\underset{|}{C}}\overset{R^1}{\overset{|}{R^2}}$   EP 462,830

SUMMARY OF THE INVENTION

The present invention relates to heteroaryl quinolines having activity as leukotriene biosynthesis inhibitors, to methods for their preparation, and to methods and pharmaceutical formulations for using these compounds in mammals (especially humans).

Because of their activity as leukotriene biosynthesis inhibitors, the compounds of the present invention are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection and in preventing the formation of atherosclerotic plaques.

DETAILED DESCRIPTION OF THE INVENTION

The compounds of the present invention may be represented by the following formula I:

wherein:

$R^1$ is H, OH, lower alkyl, or lower alkoxy;

$R^2$ is H or lower alkyl, or together with $R^1$ forms a double bonded oxygen (=O);

$R^3$ is H, lower alkyl, hydroxy lower alkyl, or lower alkoxy lower alkyl, or is joined to $R^1$ to form a carbon bridge of 2 or 3 carbon atoms or a mono-oxa carbon bridge of 1 or 2 carbon atoms, said bridge optionally containing a double bond;

$R^4$ is H or lower alkyl;

$R^5$ is H, OH, lower alkyl, or lower alkoxy;

$R^6$ is H, OH, lower alkyl, lower alkoxy, lower alkylthio, or lower alkylcarbonyloxy;

$R^7$, $R^{14}$, and $R^{16}$ is each independently H, halogen, lower alkyl, hydroxy, lower alkoxy, $CO_2R^{13}$, $CF_3$, CN, $COR^{15}$, or $C(R^{15})_2OH$;

$R^8$ is H, oxo, thioxo, halogen, CN, $CF_3$, lower alkoxy, $(R^{14})_2$-benzyloxy, $COR^{13}$, or $CO_2R^{13}$;

$R^9$ and $R^{10}$ is each independently H, alkyl, aryl $(R^{14})_2$, aryl$(R^{14})_2$-CO, or aryl$(R^{14})_2$-lower alkyl wherein aryl is a 5-membered aromatic ring containing one O, S, or N and 0–3 carbon atoms are replaced by N; a dihydro 5-membered aromatic ring containing one O, S, or N and 0≅3 carbon atoms are replaced by N; a 6-membered aromatic ring wherein 0–3 carbon atoms are replaced by N; 2- or 4-pyranone; 2- or 4-pyridinone; or a bicyclic 8-, 9-, or 10-membered aromatic ring wherein 0–2 carbon atoms are replaced by either O or S or a combination thereof and 0–3 carbon atoms are replaced by N;

$R^{11}$ and $R^{12}$ is each H or together form a bond;

$R^{13}$ is H or lower alkyl;

$R^{15}$ is H or lower alkyl, or two $R^{15}$ groups attached to the same carbon may form a saturated ring of 3 to 8 members;

$X^1$ is O, S, S(O), S(O)$_2$, or $CH_2$;

$X^2$ is O, S, or $C(R^{15})_2$;

$X^3$ is $C(R^{15})_2O$, $C(R^{15})_2S$, or $[C(R^{15})_2]_n$;

Ar is arylene-$(R^{16})_2$, wherein arylene is a 5-membered aromatic ring containing one O or S and with 0–2 carbon atoms replaced by N; a 5-membered aromatic ring containing 1–3 nitrogen atoms; a 6-membered aromatic ring wherein 0–3 carbon atoms are replaced by N; 2- or 4-pyranone; or 2- or 4-pyridinone;

m is 0 or 1;

n is 1 or 2;

A is C or N, with the proviso that one and only one A is N;

or a pharmaceutically acceptable salt thereof.

A preferred embodiment of the present invention is represented by Formula Ia:

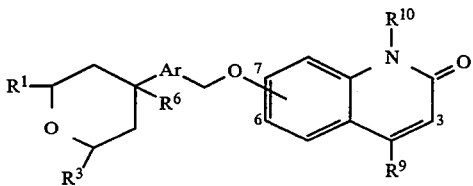

wherein:

R¹ and R³ is each independently H or CH₃, or together are —CH₂CH₂—, —CH₂O—, or —OCH₂—;

R⁶ is OH or OMe;

R⁹ is H, Me, Ph, 3-Fu, or 3-Th;

R¹⁰ is H, Me, Et, c-Hex, Ph, PhCH₂, PyCH₂, TzCH₂, or naphthyl-CH₂;

Ar is 3-Phe, 5,3-Pye, 4,2-Pye, 2,4-Pye, 6,2-Pye, or 2,4-Tze; and the ArCH₂O link is attached at position 6 or 7 of the quinolinone.

Another preferred embodiment of the present invention is represented by Formula Ib:

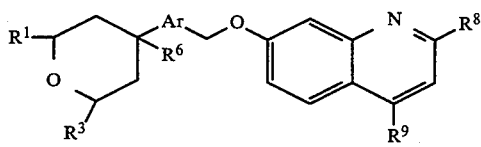

wherein:

R¹ and R³ is each H or together are —CH₂O—;

R⁶ is OH or OMe;

R⁸ is H, OMe, CN, or PhCH₂O;

R⁹ is Ph, 3-Fu, or 3-Th; and

Ar is 3-Phe or 6,2-Pye.

Another preferred embodiment of the present invention is represented by Formula Ic:

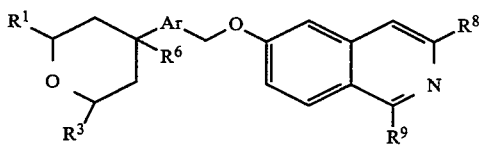

wherein:

R¹ and R³ is each H or together are —CH₂O—;

R⁶ is OH or OMe;

R⁸ is CO₂Me or CO₂H;

R⁹ is Ph, 3-Fu, or 3-Th; and

Ar is 3-Phe or 6,2-Pye.

Definitions

The following abbreviations have the indicated meanings:

| | |
|---|---|
| Ac = | acetyl |
| AIBN = | 2,2′-azobisisobutyronitrile |
| Bn = | benzyl |
| CSA = | camphor sulfonic acid |
| DCC = | 1,3-dicyclohexycarbodiimide |
| DDQ = | 2,3-dichloro-5,6-dicyano-1,4-benzoquinone |
| DHP = | 3,4-dihydro-2H-pyran |
| DIBAL = | diisobutylaluminum hydride |
| DIPHOS = | 1,2-Bis(diphenylphosphino)ethane |
| DMAP = | 4-(dimethylamino)pyridine |
| DMF = | N,N-dimethylformamide |
| DMSO = | dimethyl sulfoxide |
| Et₃N = | triethylamine |
| Fu = | 2- or 3- furyl |
| Fur = | furandiyl |
| KHMDS = | potassium hexamethyldisilazane |
| LDA = | lithium diisopropylamide |
| Ms = | methanesulfonyl = mesyl |
| MsO = | methanesulfonate = mesylate |
| NBS = | N-bromosuccinimide |
| NCS = | N-chlorosuccinimide |
| NSAID = | non-steroidal anti-inflammatory drug |
| PCC = | pyridinium chlorochromate |
| PDC = | pyridinium dichromate |
| Ph = | phenyl |
| Phe = | benzenediyl |
| Py = | 2-, 3- or 4- pyridyl |
| Pye = | pyridinediyl |
| RIA = | radioimmunoassay |
| r.t. = | room temperature |
| rac. = | racemic |
| Super-Hydride = | lithium triethylborohydride |
| t-BOC = | t-butyloxycarbonyl |
| TFA = | trifluoroacetic acid |
| TFAA = | trifluoroacetic acid anhydride |
| TMSCl = | trimethylsilyl chloride |
| Tf = | trifluoromethanesulfonyl = triflyl |
| TfO = | trifluoromethanesulfonate = triflate |
| Th = | 2- or 3-thienyl |
| THF = | tetrahydrofuran |
| Thz = | 2-, 4- or 5-thiazolyl |
| Thz-H = | 4,5-dihydrothiazolyl |
| Thi = | thiophenediyl |
| Ts = | p-toluenesulfonyl = tosyl |
| TsO = | p-toluenesulfonate = tosylate |
| Tz = | 1H (or 2H)-tetrazol-5-yl |
| Tze = | thiazoldiyl |
| C₃H₅ = | allyl |
| Alkyl group abbreviations | |
| Me = | methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | cyclobutyl |
| c-Pen = | cyclopentyl |
| c-Hex = | cyclohexyl |

Alkyl is intended to include linear, branched, and cyclic structures and combinations thereof.

"Alkyl" includes "cycloalkyl" and "lower alkyl" and extends to cover carbon fragments having up to 20 carbon atoms. Examples of alkyl groups include octyl, nonyl, undecyl, dodecyl, tridecyl, tetradecyl, pentadecyl, eicosyl, 3,7-diethyl-2,2-dimethyl-4-propylnonyl, cyclopropyl, cyclohexyl, cyclododecyl, adamantyl, and the like.

"Lower alkyl" includes "lower cycloalkyl" and means alkyl groups of from 1 to 7 carbon atoms. Examples of lower alkyl groups include methyl, ethyl, propyl, isopropyl, butyl, s- and t-butyl, pentyl, hexyl, heptyl, cyclopropyl, cyclohexyl, and the like.

"Cycloalkyl" includes "lower cycloalkyl" and means a hydrocarbon, containing one or more rings of from 3 to 12 carbon atoms, with the hydrocarbon having up to a total of 20 carbon atoms. Examples of cycloalkyl groups are cyclopropyl, cyclopentyl, cycloheptyl, adamantyl, cyclododecylmethyl, 2-ethyl-1-bicyclo[4.4.0]decyl, and the like.

"Lower cycloalkyl" means a hydrocarbon containing one or more rings of from 3 to 7 carbon atoms, with the hydrocarbon having up to a total of 7 carbon atoms.

Examples of lower cycloalkyl groups are cyclopropyl, cyclopropylmethyl, cyclobutyl, 2-cyclopentylethyl, cycloheptyl, bicyclo[2.2.1]hept-2-yl, and the like.

"Lower alkoxy" means alkoxy groups of from 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

"Lower alkylthio" means alkylthio groups of from 1 to 7 carbon atoms of a straight, branched, or cyclic configuration. Examples of lower alkylthio groups include methylthio, propylthio, isopropylthio, cycloheptylthio, etc. By way of illustration, the propylthio group signifies —$SCH_2CH_2CH_3$.

"Lower alkylcarbonyloxy" means alkylcarbonyloxy groups of from 1 to 8 carbon atoms of a straight, branched, or cyclic configuration. Examples of lower alkylcarbonyloxy groups are carbomethoxy and carboethoxy. By way of illustration, the $CO_2$-c-Hex group signifies carbocyclohexyloxy.

Halogen includes F, Cl, Br, and I.

It is intended that the definitions of any substituent (e.g., $R^{14}$, $R^{15}$, etc.) in a particular molecule be independent of its definitions elsewhere in the molecule. Thus, $C(R^{15})_2$ represents RHH, $RHCH_3$, $RCH_3CH_3$, etc.

Examples of Ar are furan, thiophene, oxazole, thiazole, 1,3,4-oxadiazole, 1,3,4-thiadiazole, 1,2,5-oxadiazole, 1,2,5-thiadiazole, pyrrole, imidazole, 1,3,4-triazole, benzene, pyridine, pyrazine, pyrimidine, pyridazine, 1,2,3-triazine, 1,2,4-triazine, and 1,3,5-triazine.

Examples of aryl within $R^9$ and $R^{10}$ are furan, thiophene, oxazole, thiazole, isoxazole, isothiazole, 1,3,4-oxadiazole, 1,3,4-thiadiazole, 1,2,5-oxadiazole, 1,2,5-thiadiazole, pyrrole, pyrazole, imidazole, 1,3,4-triazole, tetrazole, benzene, pyridine, pyrazine, pyrimidine, pyridazine, 1,2,3-triazine, 1,2,4-triazine, 1,3,5-triazine, thieno[2,3-b]furan, thieno[3,2-b]pyrrole, indole, benzofuran, benzothiophene, benzimidazole, benzoxazole, benzothiazole, benzo[2,1,3]thiadiazole, furano[3,2-b]pyridine, naphthalene, quinoline, isoquinoline, quinoxaline, quinazoline, cinnoline, phthalazine, 1,8-naphthyridine, and the like.

The term "arylene-$(R^{16})_2$" means an arylene group substituted by two $R^{16}$ substituents.

The rings formed when two $R^{15}$ groups join include cyclopropane, cyclobutane, cyclopentane, cyclohexane, cycloheptane, cyclooctane, oxetane, tetrahydrofuran, tetrahydropyran, tetrahydrothiophene, tetrahydrothiopyran, pyrrolidine, piperidine, morpholine, thiamorpholine, and piperazine.

Optical Isomers—Diastereomers—Geometric Isomers

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

Salts

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

Utilities

The ability of the compounds of Formula I to inhibit biosynthesis of the leukotrienes makes them useful for preventing or reversing the symptoms induced by the leukotrienes in a human subject. This inhibition of the mammalian biosynthesis of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflamation such as arthritis or inflammatory bowel disease, 4) pain, 5) skin disorders such as a topic eczema, and the like, 6) cardiovascular disorders such as angina, formation of atherosclerotic plaques, myocardial ischemia, hypertension, platelet aggregation, and the like, 7) renal insufficiency arising from ischaemia induced by immunological or chemical (cyclosporin) etiology; 8) migraine or cluster headache, 9) ocular conditions such as uveitis, 10) hepatitis resulting from chemical, immunological or infectious stimuli, 11) trauma or shock states such as burn injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, 15) cholecystitis, and 16) multiple sclerosis.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure. The compounds also act as inhibitors of rumor metastasis and exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions, and the like.

Two assays can be used to measure cytoprotective ability. These assays are: (A) an ethanol-induced lesion assay, and (B) an indomethacin-induced ulcer assay and are described in EP 140,684.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

The exact mount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

Pharmaceutical Compositions

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the an of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of compound I in suitable propellants, such as fluorocarbons or hydrocarbons.

Suitable topical formulations of Compound I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I | 25 |

-continued

| | |
|---|---|
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liquid Concentrate | 1.2 mg |
| Trichlorofluoromethane, NF | 4.025 g |
| Dichlorodifluoromethane, NF | 12.15 g |

Combinations With Other Drugs

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the oxicams; and
(5) the biphenylcarboxylic acid derivatives;
or a pharmaceutically acceptable salt thereof.

The propionic acid derivatives which may be used comprise: aminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO—Na+ or —CH$_2$CH$_2$COO—Na+), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac. Structually related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —$CH_2COOH$ group (which optionally can be in the form of a pharmaceutically acceptable salt group, e.g. —$CH_2COO-Na^+$), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

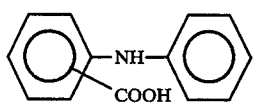

which can bear a variety of substituents and in which the free —COOH group can be in the form of a pharmaceutically acceptable salt group, e.g., —$COO-Na^+$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

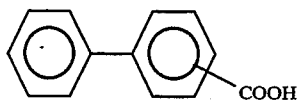

which can bear a variety of substituents and in which the free —COOH group can be in the form of a pharmaceutically acceptable salt group, e.g., —$COO-Na^+$.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

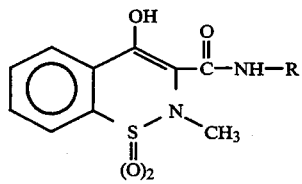

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid and ufenamate.

The following NSAIDs, designated by company code number (see e.g., Pharmaprojects), may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDs are acetyl salicylic acid, diclofenac, fenbufen, fenoprofen, flurbiprofen, ibuprofen, ketoprofen, naproxen, phenylbutazone, piroxicam, sulindac and tolmetin.

Pharmaceutical compositions comprising the Formula I compounds may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058,785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the Formula I may also be advantageously combined with an $H_1$- or $H_2$-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a K+/H+ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in *Nature,* Vol. 316, pages 126-131, 1985, and the like. Each of the references referred to in this paragraph is hereby incorporated herein by reference.

Other advantageous pharmaceutical compositions comprise the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

Methods of Synthesis

Compounds of Formula I of the present invention may be prepared according to the synthetic routes outlined in Schemes I to V and by following the methods described herein.

Scheme I

The quinoline 1A of Scheme I may be prepared in a multi-step sequence from an appropriately substituted aniline II. The amine II is firstly converted to the amide III by heating with an appropriate β-keto ester. The cyclization of the amide III to provide IV is achieved by heating in an aqueous acid such as phosphoric acid. From this reaction, the side product V may be obtained in varying amounts. Alternatively, the lactam IV can be obtained from the amide VI by cyclization in the presence of a Lewis acid such as aluminum chloride. This lactam VI can be obtained from II by treatment with an appropriate acid chloride. The amide IV is converted to quinolinone VII by treatment with a base, such as sodium hydride, in an organic solvent, such as DMF, followed by the addition of an alkylating agent, $R^{10}$-hal. The demethylation of quinolinone VII is achieved under acidic conditions, such as heating with pyridine hydrochloride, leading to VIII. Coupling of the phenol VIII with the appropriate benzylic derivative X in an organic solvent such as DMF using an inorganic base such as $K_2CO_3$ provides compounds of Formula 1A of the present invention. Alternatively, s coupling of the phenol VIII with the appropriate benzylic alcohol such as 3-[4-(4-hydroxy)tetrahydropyranyl]-5-hydroxymethylpyridine in an organic solvent such as THF by treatment with a phosphine and dialkyl azodicarboxylate, such as triphenylphosphine and di-t-butylazodicarboxylate, provides compounds of Formula 1A of the present invention. An alternative route may also be used to prepare the compounds of Formula 1A. The methyl ether IV is first converted to the phenol IX by demethylation in a manner similar to that described for the conversion of VII to VIII. Treatment of the phenol IX with the appropriate benzylic compound X, in a manner similar to that described for the conversion of VIII to 1A, followed by alkylation in a manner similar to that described for the conversion of IV to VII, provides compounds of Formula 1A of the present invention.

Scheme II

The quinolinone 1B of Scheme II may be prepared in a multi-step sequence, from an appropriately substituted quinoline XI. The quinoline XI is converted to the N-oxide XII by treatment with an oxidizing agent such as m-chloroperbenzoic acid in an organic solvent such as $CH_2Cl_2$. Conversion of XII to the quinolinone XIII is accomplished by treatment of XII with an anhydride, such as trifluoroacetic anhydride in an organic solvent such as DMF. The quinolinone XIII is then converted into compounds of Formula 1B of the present invention by procedures similar to those described for the conversion of IV to 1A in Scheme I.

Scheme III

The quinoline 1C of Scheme III may be prepared in a multi-step sequence, from quinolinone IV of Scheme I or quinolinone XIII of Scheme II. The quinolinone is converted into the quinoline XVII by a two-step procedure involving reduction to the 1,2-dihydroquinoline XVI with a reducing agent, such as lithium aluminum hydride in an organic solvent such as THF, followed by treatment with an oxidizing agent, such as ceric ammonium nitrate. The quinoline XVII is then converted into phenol XX ($R^8$=H) using procedures similar to those described for the conversion of VII to VIII in Scheme I. Alternatively, quinoline XVII can be converted to N-oxide XVIII in a manner similar to that described for the conversion of XI into XII in Scheme II. The cyano quinoline XIX can be obtained from the N-oxide XVIII by treatment with a cyanide, such as trimethylsilyl cyanide, in the presence of a carbamyl chloride, such as N,N-dimethylcarbamyl chloride in an organic solvent such as dichloromethane. Demethylation of XIX in a manner similar to that described for the conversion of VII to VIII in Scheme I provides the intermediate XX ($R^8$=CN). The nitrile can be used for the introduction of other substituents ($R^8$=$COR^{13}$, $CO_2R^{13}$) according to standard organic procedures. Conversion of XX to compounds of Formula IC of the present invention can be accomplished by procedures similar to those described for the conversion of VIII to 1A in Scheme I.

Scheme IV

The isoquinoline 1D of Scheme IV may be prepared, in a multi-step sequence, from an appropriately substituted alkyl 2-amino-3-aryl propionate XXI. The amine is first converted to the amide XXII by treatment with an appropriate acid halide $R^9COCl$. The ester XXII is converted into the ether XXIII by transesterification with an alcohol such as methanol followed by alkylation with a methyl halide, such as iodomethane in the presence of an inorganic base such as $K_2CO_3$ in an organic solvent such as DMF. The cyclization of the amide XXIII to provide XXIV is achieved by heating with a dehydrating agent such as phosphorus pentoxide. The 3,4-dihydroisoquinoline XXIV is converted into the isoquinoline XXV by treatment with an oxidizing agent such as DDQ. Demethylation of XXV to XXVI is achieved under conditions similar to those described for the conversion of VII to VIII in Scheme I. The ester can be used for the introduction of other substituents (R⁸=CN, COR¹³) according to standard organic procedures. Conversion of XXVI to compounds of Formula 1D of the present invention can be accomplished by procedures similar to those described for the s conversion of VIII to 1A in Scheme I.

Scheme V

The quinoline 1E of Scheme V may be prepared from quinolinone 1A or 1B (R¹⁰=H) of Scheme I and Scheme II, respectively. Treatment of 1A or 1B (R¹⁰=H) with an organic halide in the presence of a silver salt such as silver carbonate in an organic solvent such as benzene provides compounds of Formula 1E of the present invention.

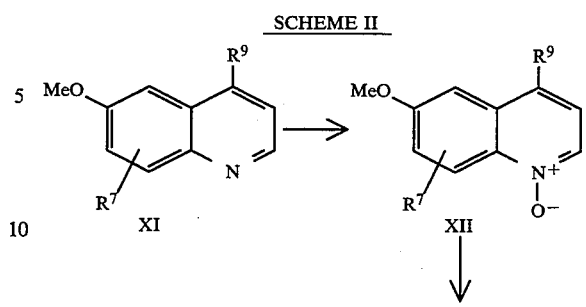

SCHEME II

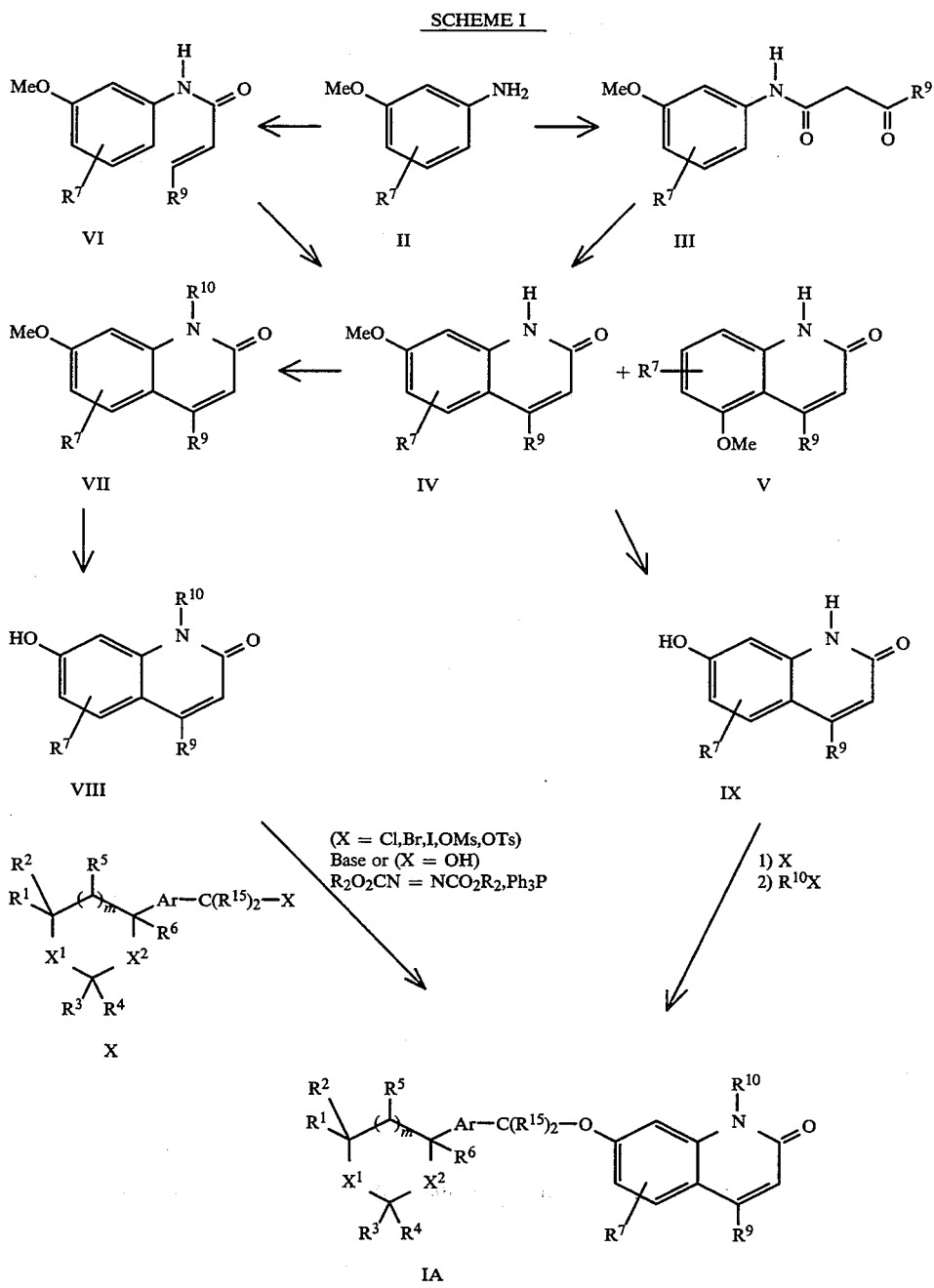

SCHEME I

-continued
SCHEME II
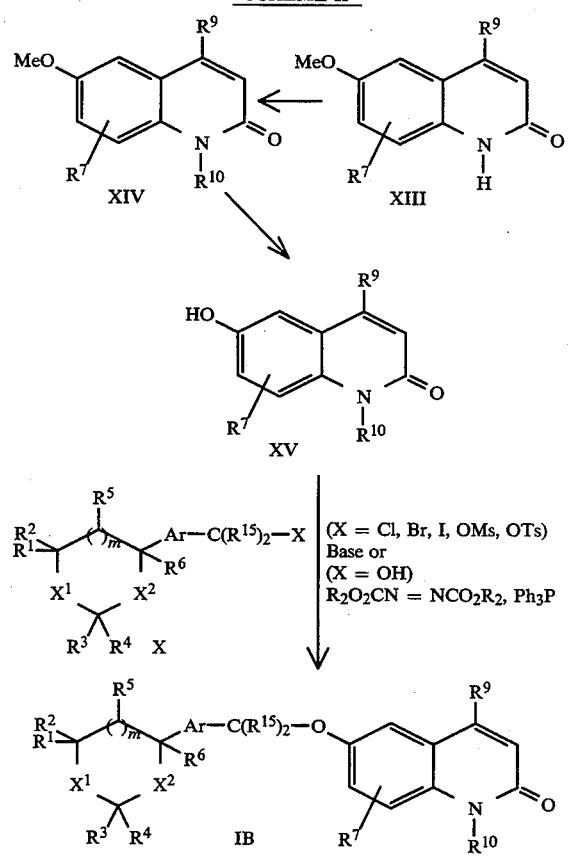
SCHEME III
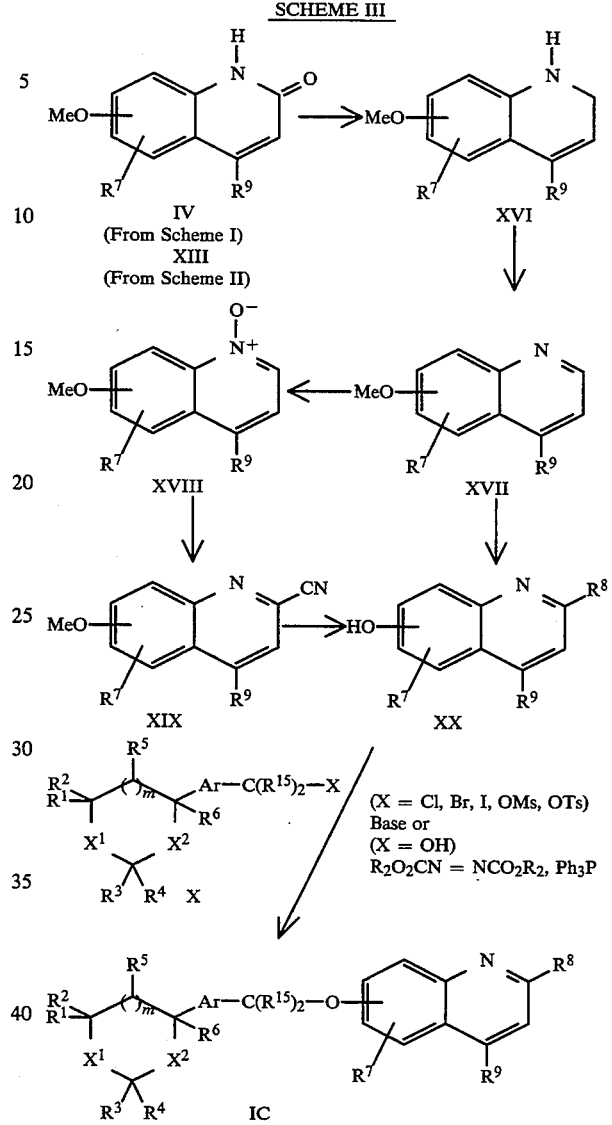
SCHEME IV
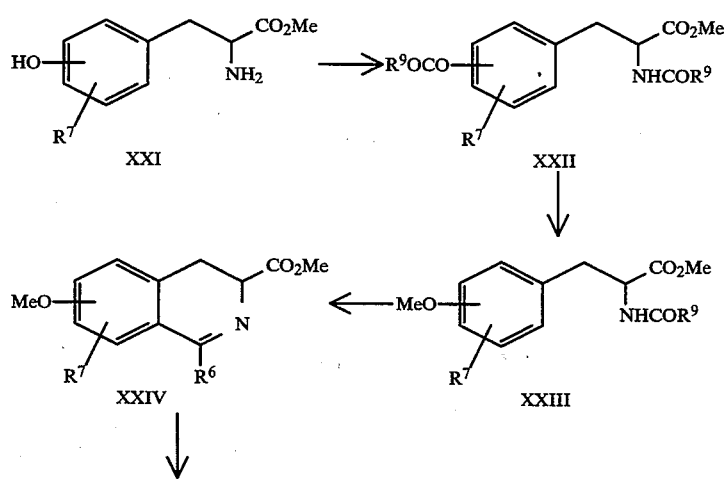

SCHEME IV

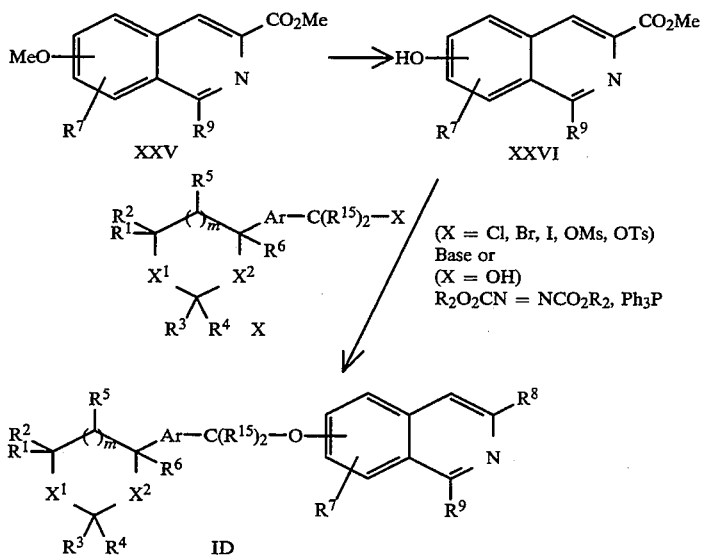

SCHEME V

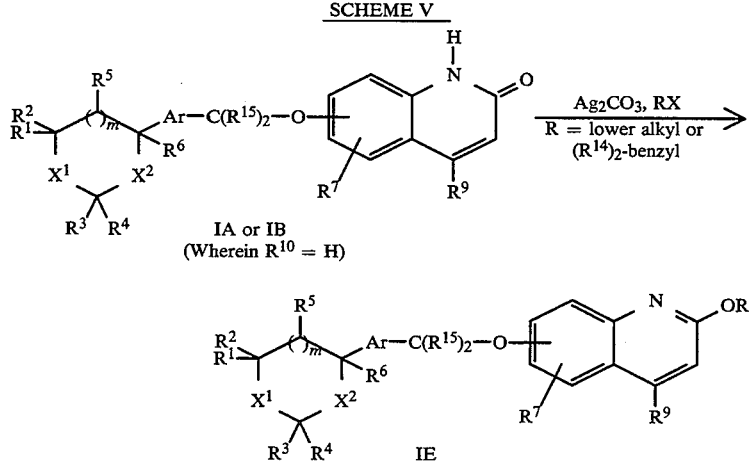

Representative Compounds

Tables 1–4 illustrate compounds of formulas Id, Ie, If, and Ig, which are representative of the present invention.

TABLE 1

Id

| Ex. | $R^1$ | $R^3$ | $R^6$ | $R^9$ | $R^{10}$ | Ar |
|---|---|---|---|---|---|---|
| 1 | H | H | OMe | Ph | H | 3-Phe |
| 2 | H | OH | Ph | | Me | 3-Phe |
| 3 | H | H | OMe | Ph | Me | 3-Phe |
| 4 | H | H | OMe | Ph | Et | 3-Phe |
| 5 | H | H | OH | Ph | $PhCH_2$ | 3-Phe |
| 6 | H | H | OMe | Ph | $PhCH_2$ | 3-Phe |
| 7 | H | H | OMe | Ph | $2\text{-}PyCH_2$ | 3-Phe |
| 8 | H | H | OMe | Ph | $4\text{-}NCPheCH_2$ | 3-Phe |
| 9 | H | H | OMe | Ph | $4\text{-}(2\text{-}MeC_3HNS)CH_2$* | 3-Phe |
| 10 | H | H | OMe | Ph | $c\text{-}HexCH_2$ | 3-Phe |

TABLE 1-continued

Id

| Ex. | $R^1$ | $R^3$ | $R^6$ | $R^9$ | $R^{10}$ | Ar |
|---|---|---|---|---|---|---|
| 11 | H | H | OMe | Ph | $1\text{-}C_{10}H_7CH_2$** | 3-Phe |
| 12 | H | H | OMe | Ph | $3\text{-}PyCH_2$ | 3-Phe |
| 13 | H | H | OMe | Ph | $3\text{-}MeO_2CPheCH_2$ | 3-Phe |
| 14 | H | H | OMe | Ph | Ph | 3-Phe |
| 15 | H | H | OH | 3-Fu | $PhCH_2$ | 3-Phe |
| 16 | H | H | OMe | 3-Fu | $PhCH_2$ | 3-Phe |
| 17 | H | H | OMe | 3-Fu | $4\text{-}ClPheCH_2$ | 3-Phe |
| 18 | —$CH_2O$— | | OH | 3-Fu | $PhCH_2$ | 3-Phe |
| 19 | H | H | OH | 3-Fu | $PhCH_2$ | 5,3-Pye |
| 20 | H | H | OH | 3-Fu | $4\text{-}FPheCH_2$ | 5,3-Pye |
| 21 | H | H | OH | 3-Fu | $4\text{-}FPheCH_2$ | 6,2-Pye |
| 22 | H | H | OH | 3-Fu | $4\text{-}ClPheCH_2$ | 6,2-Pye |
| 23 | —$CH_2O$— | | OH | 3-Fu | $PhCH_2$ | 6,2-Pye |
| 24 | H | H | OH | 3-Th | $PhCH_2$ | 3-Phe |
| 25 | H | H | OMe | 3-Th | $PhCH_2$ | 3-Phe |
| 26 | H | H | OMe | 3-Th | $3\text{-}MeO_2CPheCH_2$ | 3-Phe |

TABLE 1-continued

Structure Id: R¹–(O,R³)–ring–C(Ar,R⁶)–CH₂–O–[quinolin-2(1H)-one with R⁹ at 4-position, R¹⁰ on N]

| Ex. | R¹ | R³ | R⁶ | R⁹ | R¹⁰ | Ar |
|---|---|---|---|---|---|---|
| 27 | H | H | OMe | 3-Th | 4-MeO₂CPheCH₂ | 3-Phe |
| 28 | H | H | OMe | 3-Th | 3-(HO(Me₂)C)PheCH₂ | 3-Phe |
| 29 | H | H | OMe | 3-Th | 3-HO₂CPheCH₂ | 3-Phe |
| 30 | H | H | OMe | 3-Th | HO(Me₂)C(CH₂)₃ | 3-Phe |
| 31 | H | H | OH | 3-Th | PhCH₂ | 5,3-Pye |
| 32 | H | H | OH | 3-Th | PhCH₂ | 6,2-Pye |
| 33 | H | H | OMe | Me | PhCH₂ | 3-Phe |
| 34 | H | H | OH | Me | PhCH₂ | 5,3-Pye |
| 35 | H | H | OMe | H | PhCH₂ | 3-Phe |
| 55 | —CH₂O— | | OH | 3-Fu | 4-FPheCH₂ | 6,2-Pye |
| 56 | —CH₂O— | | OH | 3-Th | PhCH₂ | 6,2-Pye |
| 57 | —CH₂O— | | OH | 3-Th | 4-FPheCH₂ | 6,2-Pye |
| 58 | —CH₂O— | | OH | 3-Fu | 4-ClPheCH₂ | 6,2-Pye |

*2-methylthiazol-4-ylmethyl
**naphth-1-ylmethyl

TABLE 2

Structure Ie

| Ex. | R¹ | R³ | R⁶ | R⁹ | R¹⁰ | Ar |
|---|---|---|---|---|---|---|
| 36 | H | H | OMe | H | CH₃ | 3-Phe |
| 37 | H | H | OH | H | PhCH₂ | 3-Phe |
| 38 | H | H | OMe | H | PhCH₂ | 3-Phe |
| 39 | H | H | OH | H | Ph | 3-Phe |
| 40 | H | H | OMe | H | Ph | 3-Phe |

TABLE 3

Structure If

| Ex. | R¹ | R³ | R⁶ | R⁸ | R⁹ | Ar |
|---|---|---|---|---|---|---|
| 41 | H | H | OMe | OMe | Ph | 3-Phe |
| 42 | H | H | OMe | OMe | Ph | 3-Phe |
| 43 | H | H | OMe | 4-NCPheCH₂O— | Ph | 3-Phe |
| 44 | —CH₂O— | | OH | H | Ph | 6,2-Pye |
| 45 | H | H | OMe | CN | Ph | 3-Phe |
| 46 | —CH₂O— | | OH | CN | Ph | 6,2-Pye |
| 47 | H | H | OH | H | 3-Fu | 3-Phe |
| 48 | H | H | OMe | H | 3-Fu | 3-Phe |
| 49 | H | H | OH | H | 3-Th | 3-Phe |
| 50 | H | H | OMe | H | 3-Th | 3-Phe |
| 59 | —CH₂O— | | OH | CN | 3-Fu | 6,2-Pye |
| 60 | —CH₂O— | | OH | CN | 3-Th | 6,2-Pye |
| 61 | —CH₂O— | | OH | CO-2-Thz | 3-Fu | 6,2-Pye |
| 62 | —CH₂O— | | OH | 2-Thz—H | 3-Fu | 6,2-Pye |
| 63 | —CH₂O— | | OH | H | 3-Th | 6,2-Pye |
| 64 | —CH₂O— | | OH | CN | 3-Fu | 3-Phe |
| 65 | —CH₂O— | | OH | CO-2-Thz | 3-Th | 6,2-Pye |
| 66 | —CH₂O— | | OH | 2-Thz—H | 3-Th | 6,2-Pye |

TABLE 4

Structure Ig

| Ex. | R¹ | R³ | R⁶ | R⁸ | R⁹ | Ar |
|---|---|---|---|---|---|---|
| 52 | H | H | OMe | CO₂Me | Ph | 3-Phe |
| 53 | H | H | OH | CO₂Me | Ph | 3-Phe |
| 54 | H | H | OMe | CO₂H | Ph | 3-Phe |
| 67 | —CH₂O— | | OH | CN | 3-Fu | 6,2-Pye |
| 68 | —CH₂O— | | OH | CN | 3-Th | 6,2-Pye |
| 69 | —CH₂O— | | OH | CN | Ph | 6,2-Pye |

Assays for Determining Biological Activity

Compounds of Formula I can be tested using the following assays to determine their mammalian leukotriene biosynthesis inhibiting activity.

Human 5-Lipoxygenase Inhibitor Screen

Objective of the Assay: The objective of the assay is to select agents which specifically inhibit the activity of human 5-lipoxygenase using a 100,000×g supernatant fraction prepared from insect cells infected with recombinant baculovirus containing the coding sequence for human 5-lipoxygenase. Enzyme activity is measured spectrophotometrically from the optimal rate of conjugated diene formation ($A_{234}$) measured after the incubation of the enzyme with arachidonic acid in the presence of ATP, calcium ions and phosphatidylcholine.

Description of Procedure: The activity of 5-lipoxygenase is measured using a spectrophotometric assay and recombinant human 5-lipoxygenase as a source of enzyme. The 100,000×g fraction from S19 cells infected with the recombinant baculovirus rvH5LO(8-1 ) containing the coding region sequence for human 5-lipoxygenase is prepared as described by Denis et al. (J. Biol. Chem., 266, 5072–5079 (1991 )). The enzymatic activity is measured, using a spectrophotometric assay from the optimal rate of conjugated diene formation ($A_{234}$) using the procedure described by Riendeau et al. (Biochem. Pharmacol. 38, 2323–2321, (1989)) with minor modifications. The incubation mixture contains 50 mM sodium phosphate pH 7.4, 0.2 mM ATP, 0.2 mM CaCl₂, 20 μM arachidonic acid (5 μL from a 100-fold concentrated solution in ethanol), 12 μg/mL phosphatidylcholine, an aliquot of the 100,000×g fraction (2–10 μL) and inhibitor (0.5 mL final volume). Inhibitors are added as 500-fold concentrated solutions in DMSO. Reactions are initiated by the addition of an aliquot of the enzyme preparation and the rate of conjugated diene formation is followed for 2 minutes at room temperature. The reactions are performed in semi-micro cuvettes (0.7 mL capacity, 10 mm path length and 4 mm internal width) and the absorbance changes are recorded with a Hewlett-Packard diode array spectrophotometer (HP 8452A) connected to the ChemStation using UV/VIS Kinetics Software (Hewlett-Packard). Enzymatic activity is calculated from the optimal rate of the reaction by a linear fit of the variation of $A_{234}$ during the first twenty seconds using the least square method for the equation $A_{234} = V_o t + A_o$ where $V_o$ is the rate, t is the time, and $A_o$ is the absorbance at zero time. The results are expressed as percentages of inhibition of the reaction rate relative to controls (typically between 0.15–0.21 AU/min) containing the DMSO vehicle.

Rat Peritoneal Polymorphonuclear (PMN) Leukocyte Assay

Rats under ether anesthesia are injected (i.p.) with 8 mL of a suspension of sodium caseinate (6 grams in ca. 50 mL water). After 15–24 hr. the rats are sacrificed ($CO_2$) and the cells from the peritoneal cavity are recovered by lavage with 20 mL of buffer (Eagles MEM containing 30 mM HEPES adjusted to pH 7.4 with NaOH). The cells are pelleted (350×g, 5 min.), resuspended in buffer with vigorous shaking, filtered through lens paper, recentrifuged and finally suspended in buffer at a concentration of 10 cells/mL. A 500 $\mu$L aliquot of PMN suspension and test compound are preincubated for 2 minutes at 37° C., followed by the addition of 10 $\mu$M calcium ionophore A-23187. The suspension is stirred for an additional 4 minutes then bioassayed for $LTB_4$ content by adding an aliquot to a second 500 $\mu$L portion of the PMN at 37° C. The $LTB_4$ produced in the first incubation causes aggregation of the second PMN, which is measured as a change in light transmission. The size of the assay aliquot is chosen to give a submaximal transmission change (usually −70%) for the untreated control. The percentage inhibition of $LTB_4$ formation is calculated from the ratio of transmission change in the sample to the transmission change in the compound-free control.

Human Polymorphonuclear (PMN) Leukocyte $LTB_4$ Assay

A. Preparation of Human PMN. Human blood is obtained by antecubital venepuncture from consenting volunteers who have not taken medication within the previous 7 days. The blood is immediately added to 10% (v/v) trisodium citrate (0.13M) or 5% (v/v) sodium heparin (1000 IU/mL). PMNs are isolated from anticoagulated blood by dextran sedimentation of erythrocytes followed by centrifugation through Ficoll-Hypaque (specific gravity 1.077), as described by Boyum (*Scand. J. Clin. Lab. Invest.*, 21 (Supp 97), 77 (1968)). Contaminating erythrocytes are removed by lysis following exposure to ammonium chloride (0.16M) in Tris buffer (pH 7.65), and the PMNs are resuspended at $5 \times 10^5$ cells/mL in HEPES (15 mM)-buffered Hanks balanced salt solution containing $Ca^{2+}$ (1.4 mM) and $Mg^{2+}$ (0.7 mM), pH 7.4.

B. Generation and Radioimmunoassay of $LTB_4$. PMNs (0.5 mL; $2.5 \times 10^5$ cells) are placed in plastic tubes and incubated (37° C., 2 min) with test compounds at the desired concentration or vehicle (DMSO, final concentration 0.2%) as control. The synthesis of $LTB_4$ is initiated by the addition of calcium ionophore A23187 (final concentration 10 $\mu$M) or vehicle in control samples and allowed to proceed for 5 minutes at 37° C. The reactions are then terminated by the addition of cold methanol (0.25 mL) and samples of the entire PMN reaction mixture are removed for radioimmunoassay of $LTB_4$.

Samples (50 $\mu$L) of authentic $LTB_4$ of known concentration in radioimmunoassay buffer (R/A) buffer (potassium phosphate 1 mM; disodium EDTA 0.1 mM; Thimerosal 0.025 mM; gelatin 0.1%, pH 7.3) or PMN reaction mixture diluted 1:1 with RIA buffer are added to reaction tubes. Thereafter [$^3$H]-$LTB_4$ (10 nCi in 100 $\mu$L RIA buffer) and $LTB_4$-antiserum (100 $\mu$L of a 1:3000 dilution in RIA buffer) are added and the tubes vortexed. Reactants are allowed to equilibrate by incubation overnight at 4° C. To separate antibody-bound from free $LTB_4$, aliquots (50 $\mu$L) of activated charcoal (3% activated charcoal in RIA buffer containing 0.25% Dextran T-70) are added, the tubes vortexed, and allowed to stand at room temperature for 10 minutes prior to centrifugation (1500×g; 10 min; 4° C.). The supernatants containing antibody-bound $LTB_4$ are decanted into vials and Aquasol 2 (4 mL) is added. Radioactivity is quantified by liquid scintillation spectrometry. The specificity of the antiserum and the sensitivity of the procedure have been described by Rokach et al, *Prostaglandins Leukotrienes and Medicine*, 13, 21 (1984). The amount of $LTB_4$ produced in test and control samples is calculated. Inhibitory dose-response curves are constructed using a four-parameter algorithm and from these the $IC_{50}$ values are determined.

Human Whole Blood Assay in Vitro for $LTB_4$ Production

Fresh blood is collected in heparinized tubes by venipuncture from human volunteers. A 500 $\mu$L aliquot is incubated with one of the test compounds at final concentrations varying from 3 nM to 3 mM at 37° C. for 15 min. Drug stock solutions are made up in DMSO and 1 $\mu$L of the stock solution is added to each assay tube. The blood is then incubated with A23187 (in 5 $\mu$L autologous plasma, 25 $\mu$M final concentration) at 37° C. for 30 min. At the end of incubation, plasma is obtained (12,000×g, 15 min) and a 100 $\mu$L aliquot is added to 400 $\mu$L methanol for protein precipitation. The mixture is vortexed, centrifuged and the supernatant stored at −70° C. until assayed for $LTB_4$ by standard RIA.

Asthmatic Rat Assay

Rats are obtained from an inbred line of asthmatic rats. Both female (190–250 g) and male (260–400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate is supplied by Sandoz Ltd., Basel.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a DeVilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Buxco Electronics preamplifier (Buxco Electronics Inc., Sharon, Conn.). The preamplifier is connected to a Beckman Type R Dynograph and to a Buxco computer consisting of waveform analyser, Data Acquisition Logger with special software. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 mL of a suspension containing 1 mg EA and 200 mg aluminum hydroxide in saline. They are used between 5 days 12 and 24 post sensitization. In order to eliminate the serotonin component of the response, rats are pretreated intravenously 5 minutes prior to aerosol challenge with 3.0 µg/kg of methysergide. Rats are then exposed to an aerosol of 3% EA in saline for exactly 1 minute, then their respiratory profiles are recorded for a further 30 minutes. The duration of continuous dyspnea is measured by the Buxco computer.

Compounds are generally administered either orally 2–4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. The activity of compounds is determined in terms of their ability to decrease the duration of antigen-induced dyspnea in comparison with a group of vehicle-treated controls. Usually, a compound is evaluated at a series of doses and an $ED_{50}$ is determined. This is defined as the dose (mg/kg) which would inhibit the duration of symptoms by 50%. Cl Pulmonary Mechanics in Trained Conscious Squirrel Monkeys The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1% methocel solution (methylcellulose, 65 HG, 400 cps) and given in a volume of 1 mL/kg body weight. For aerosol administration of compounds, a DeVilbiss ultrasonic nebulizer is utilized. Pretreatment periods vary from 5 minutes to 4 hours before the monkeys are challenged with aerosol doses of either leukotriene D4 ($LTD_4$) or Ascaris suum antigen, 1:25 dilution.

Following challenge, each minute of data is calculated by computer as a percent change from control values for each respiratory parameter including airway resistance ($R_L$) and dynamic compliance ($C_{dyn}$). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of $LTD_4$ or Ascaris antigen response by the test compound. For statistical analysis, paired t-test is used. (References: McFarlane, C. S. et al., Prostaglandins, 28, 173–182 (1984) and McFarlane, C. S. et al., Agents Actions, 22, 63–68 (1987).)

Prevention of Induced Bronchoconstriction in Allergic Sheep

A. Rationale. Certain allergic sheep with known sensitivity to a specific antigen (Ascaris suum) respond to inhalation challenge with acute and late bronchial responses. The time course of both the acute and the late bronchial responses approximates the time course observed in asthmatics and the pharmacological modification of both responses is similar to that found in man. The effects of antigen in these sheep are largely observed in the large airways and are conveniently monitored as changes in lung resistance or specific lung resistance.

B. Methods. Animal Preparation: Adult sheep with a mean weight of 35 kg (range, 18 to 50 kg) are used. All animals used meet two criteria: a) they have a natural cutaneous reaction to 1:1,000 or 1:10,000 dilutions of Ascaris suum extract (Greer Diagnostics, Lenois, N.C.) and b) they have previously responded to inhalation challenge with Ascaris suum with both an acute bronchoconstriction and a late bronchial obstruction (W. M. Abraham, et al., Am. Rev. Resp. Dis., 128, 839–44 (1983)).

Measurement of Airway Mechanics: The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one mL of air), which is positioned such that inspiration produces a negative pressure deflection with clearly discernible cardiogenic oscillations. Lateral pressure in the trachea is measured with a sidehole catheter (inner dimension, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). For the measurement of pulmonary resistance ($R_L$), the maximal end of the nasotrachel tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP-11 Digital computer (Digital Equipment Corp., Maynard, Mass.) for on-line calculation of $R_L$ from transpulmonary pressure, respiratory volume obtained by integration and flow. Analysis of 10–15 breaths is used for the determination of $R_L$. Thoracic gas volume ($V_{tg}$) is measured in a body plethysmograph, to obtain specific pulmonary resistance ($SR_L = R_L \cdot V_{tg}$).

Aerosol Delivery Systems: Aerosols of Ascaris Suum extract (1:20) are generated using a disposable medical nebulizer (Raindrop®, Puritan Bennett), which produces an aerosol with a mass median aerodynamic diameter of 6.2 µM (geometric standard deviation, 2.1) as determined by an electric size analyzer (Model 3030; Thermal Systems, St. Paul, Minn.). The output from the nebulizer is directed into a plastic t-piece, one end of which is attached to the nasotracheal tube, the other end of which is connected to the inspiratory part of a Harvard respirator. The aerosol is delivered at a tidal volume of 500 mL of a rate of 20 per minute. Thus, each sheep receives an equivalent dose of antigen in both placebo and drug trials.

Experimental Protocol: Prior to antigen challenge baseline s measurements of $SR_L$ are obtained, infusion of the test compound is started 1 hr prior to challenge, the measurement of $SR_L$ repeated and then the sheep undergoes inhalation challenge with *Ascaris suum* antigen. Measurements of $SR_L$ are obtained immediately after antigen challenge and at 1, 2, 3, 4, 5, 6, 6.5, 7, 7.5, and 8 hrs after antigen challenge. Placebo and drug tests are separated by at least 14 days. In a further study, sheep are given a bolus dose of the test compound followed by an infusion of the test compound for 0.5–1 hr prior to Ascaris challenge and for 8 hrs after Ascaris as described above.

Statistical Analysis: A Kruskal-Wallis one way ANOVA test is used to compare the acute immediate responses to antigen and the peak late response in the controls and the drug-treated animals.

The invention is further defined by reference to the following examples, which are intended to be illustrative and not limiting. Unless stated otherwise:

(i) all operations were carried out at room or ambient temperature, that is, at a temperature in the range 18°–25° C.;

(ii) evaporation of solvent was carried out using a rotary evaporator under reduced pressure (600–4000 pascals: 4.5–30 mm. Hg) with a bath temperature of up to 60° C.;

(iii) the course of reactions was followed by thin layer chromatography (TLC) and reaction times are given for illustration only;

(iv) melting points are uncorrected and "d" indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry, or microanalytical data;

(vi) yields are given for illustration only;

(vii) when given, NMR data are in the form of delta (δ) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

PREPARATION OF BENZYL HALIDES

Halide 1: 3-[4-(4-Methoxy)tetrahydropyranyl]benzyl bromide

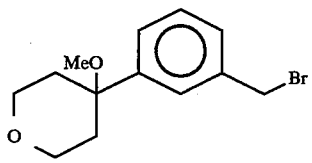

Step 1: 3-[4-(4-Hydroxy)tetrahydropyranyl]toluene

To a solution of 3-bromotoluene (24.3 mL; Aldrich) in THF (250 mL) stirred at −78° C. was added a solution of n-BuLi in hexane (1.75M; 114 mL; Aldrich). After 45 min., the resulting white suspension was treated with a solution of tetrahydropyran-4-one (18.5 mL; Aldrich) in THF (125 mL). After 45 min. at −78° C., the mixture was stirred for 1.5 hr. at r.t. Saturated aqueous NH₄Cl was then added and the organic phase separated. The aqueous phase was extracted with EtOAc. The combined organic phases were washed with brine, dried (MgSO₄) and evaporated. Flash chromatography of the residue (silica gel; hexane/EtOAc (1:1)) followed by crystallization in hexane/EtOAc afforded the title compound as a white solid.

Step 2: 3-[4-(4-Methoxy)tetrahydropyranyl]toluene

To a 0° C. solution of the alcohol from Step 1 (38 g) in DMF (300 mL) were added NaH (60% in mineral oil; 16 g) and methyl iodide (31 mL). The mixture was stirred under nitrogen at r.t. for 15 hr. before H₂O (1 μL) was added. The aqueous phase was extracted with EtOAc and the combined organic phases were washed with brine, dried (MgSO₄) and evaporated. Flash chromatography of the residue (silica gel; hexane/EtOAc (4:1) yielded the title ether as a colorless liquid.

Step 3: 3-[4-(4-Methoxy)tetrahydropyranyl]benzyl bromide

A mixture of the toluene (16 g) from Step 2, N-bromosuccinimide (14.6 g) and azoisobutyronitrile (AIBN) (127 mg) in CCl₄ (250 mL) was refluxed for 1.5 hr. Filtration and evaporation of the filtrate gave the desired benzyl bromide.

Halide 2: 3-[4-(4-Hydroxy)tetrahydropyranyl]benzyl bromide

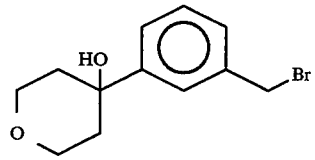

Following the procedure described for Halide 1, Step 3, but substituting 3-[4-(4-hydroxy)tetrahydropyranyl]-toluene (from Halide 1, Step 1) for 3-[4-(4-methoxy)tetrahydropyranyl]toluene, the title product was obtained as a yellow solid.

Halide 3: 3-[4-(4-Ethoxy)tetrahydropyranyl]benzyl chloride

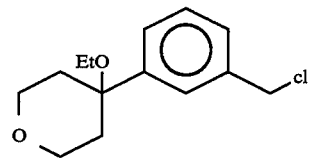

Step 1: 3-Bromobenzyl alcohol tetrahydropyranyl ether

A solution of 3-bromobenzyl alcohol (84.9 g; Aldrich), 3,4-dihydro-2H-pyran (44 g) and anhydrous p-toluene sulfonic acid (1 g) in CH₂Cl₂ (800 mL) was stirred at 5° C. for 1 hr. then at r.t. overnight. The mixture was concentrated and the residue chromatographed (5% EtOAc/hexane) to afford the title compound as an oil.

Step 2: 3-[4-(4-Hydroxy)tetrahydropyranyl]benzyl alcohol tetrahydropyranyl ether Following the procedure described for Halide 1, Step 1, but substituting the bromo compound from Step 1 for 3-bromotoluene as starting material, the title compound was obtained as an oil.

Step 3: 3-[4-(4-Ethoxy)tetrahydropyranyl]benzyl alcohol tetrahydropyranyl ether

To a solution of the alcohol (7.7 g) from Step 2 in DMF (50 mL) was added NaH (950 mg) in portions at r.t. After 1 hr, the mixture was cooled to 0° C. and ethyl iodide (3.16 mL) added. A further 1.5 mL ethyl iodide and 0.5 g NaH were added after 10 hr. and the reaction left to stir overnight. The mixture was poured into water, extracted (3×ether), washed with brine, dried and evaporated. Purification of the residue on silica gel (30% EtOAc/hexane as eluant) provided the title compound as an oil.

Step 4: 3-[4-(4-Ethoxy)tetrahydropyranyl]benzyl alcohol

To a solution of the tetrahydropyranyl ether from Step 3 (2.88 g) in MeOH (30 mL) at r.t. was added 3N HCl (15 mL) and the reaction stirred for 30 min. Ether was added to the mixture and the organic layer then washed with brine, dried and concentrated. Chromatography of the residue (40% EtOAc/hexane) afforded the title compound as an oil.

Step 5: 3-[4-(4-Ethoxy)tetrahydropyranyl]benzyl chloride

To a solution of the alcohol from Step 4 (1.78 g) and hexamethylphosphorous triamide (HMPT) in THF (35 mL) at 0° C. under nitrogen was added CCl$_4$ (1.5 mL) dropwise. After the addition was complete, the mixture was stirred for 5 min. before being concentrated in vacuo. Chromatography of the residue (30% EtOAc/hexane) afforded the title compound as an oil.

Halide 4: 3-[4-(4β-Hydroxy-2,6-dimethyl)tetrahydropyranyl]benzyl bromide

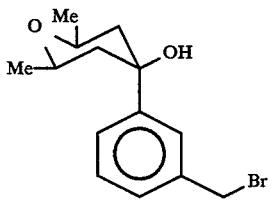

Step 1: 3-Bromo-O-tetrahydropyranylbenzyl alcohol

To a solution of 3-bromobenzyl alcohol (11.5 g; Aldrich) dissolved in CH$_2$Cl$_2$ (100 mL) at 0° C. and p-toluenesulfonic acid monohydrate (116 mg) was added DHP (6.2 mL). The resulting solution was stirred at r.t. for 3 hr. then was quenched with NH$_4$OAc. The aqueous phase was extracted with CH$_2$Cl$_2$. The combined organic phases were washed with brine, dried (MgSO$_4$) and evaporated. Flash chromatography of the residue (silica gel: hexane/EtOAc (9:1) afforded the title compound as an oil.

Step 2: 2,6-Dimethyltetrahydropyran-4-one

A solution of 2,6-dimethyl-γ-pyrone (17 g, Aldrich) in EtOH 95% (300 mL) was hydrogenated for 3 days under 70 psi. After filtration over celite, the solvent was evaporated and replaced by CH$_2$Cl$_2$. The solution was then treated with celite (30 g) and PCC (48.5 g). The suspension was stirred for 3 hr. and the reaction was diluted with Et$_2$O (300 mL) and then filtered over a pad of celite. The filtrate was evaporated to dryness and the residual solution was then chromatographed using hexane/Et$_2$O (1:1) to give the title compound.

Step 3: 3-[4-(4β-Hydroxy-2,6-dimethyl)tetrahydropyranyl]-O-tetrahydropyranylbenzyl alcohol Following the procedure described in Halide 1, Step 1, but substituting 3-bromo-O-tetrahydropyranylbenzyl alcohol (from Step 1) for 3-bromotoluene and substituting 2,6-dimethyltetrahydropyran-4-one (from Step 2) for tetrahydropyran-4-one, the title compound was obtained as a mixture of α and β isomers (30:70). Both isomers were isolated from a flash column (hexane/EtOAc) (6:4). The β-hydroxy isomer is more polar than the α-hydroxy isomer.

Step 4: 3-[4-(4β-Hydroxy-2,6-dimethyl)tetrahydropyranyl]benzyl alcohol

The β-hydroxy-THP derivative (1.0 g) from Step 3, was dissolved in EtOH (10 mL) and treated with of p-toluenesulfonic acid (30 mg). The reaction was stirred at r.t. for 90 min. The EtOH was evaporated and the resulting syrup was flash chromatographed to give the title compound.

Step 5: 3-[4-(4β-Hydroxy-2,6-dimethyl)tetrahydropyranyl]benzyl bromide

To a solution of the alcohol (183 mg) from Step 4 in CH$_2$Cl$_2$ (9 mL) was added CBr$_4$ (269 mg). The reaction was then cooled to −30° C. and DIPHOS (298 mg) was added in portions. After 10 min., the reaction was quenched with a solution (10 mL) of 10% EtOAc in hexane and without evaporation, the solvent was poured onto a silica gel column and eluted with EtOAc/hexane (3:7) affording the title compound.

Halide 5: 3-[4-(4α-Hydroxy-2,6-dimethyl)tetrahydropyranyl]benzyl bromide

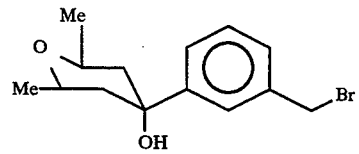

Following the procedure described in Halide 3, Steps 4–5, but substituting the α-hydroxy-THP derivative (from Halide 3, Step 3) for the β-hydroxy-THP derivative, the title product was obtained.

Halide 6: 4-Bromomethyl-2-[4-(4-hydroxy)tetrahydropyranyl]thiazole

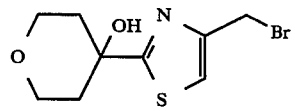

Step 1: 4-Methyl-2-[4-(4-hydroxy)tetrahydropyranyl]thiazole

To a solution of 4-methyl thiazole (990 mg) in THF (10 mL) at −78° C. there was added n-BuLi in hexanes (10 mL; 1.1M); the resulting suspension was stirred at −78° C. for 45 min. then there was added slowly a solution of tetrahydropyran-4-one (1.20 g) in THF (2 mL). The mixture was then stirred at 0° C. for 1 hr., then quenched with saturated aqueous NH$_4$Cl (8 mL), and diluted with EtOAc. The organic phase was washed (3×) with brine, dried and evaporated to a residue which was chromatographed on silica gel, eluting with a 1:1 mixture of EtOAc and hexane to afford the product as a light yellow solid.

Step 2: 4-Bromomethyl-2-[4-(4-hydroxy)tetrahydropyranyl]thiazole

Following the procedure described in Halide 1, Step 3, but substituting 4-methyl-2-[4-(4-hydroxy)tetrahydropyranyl]thiazole from Step 1, for 3-[4-(4-methoxy)-tetrahydropyranyl]toluene, the title product was obtained as a white solid.

Halide 7: 3-[4-(2,2-Dimethyl-4-ethyl-1,3-dioxalanyl)]-benzyl bromide

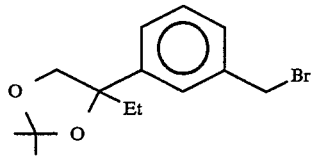

Step 1: 3-Methylpropiophenone

To a 0° C. solution of EtMgBr in Et₂O (3.0M, 570 mL, Aldrich) was slowly added m-tolunitrile (102 mL, Aldrich). After stirring at r.t. for 19 hr., benzene (300 mL) was added and the resulting mixture was cooled to 0° C. HCl (6N, 600 mL) was then slowly added. The organic phase was separated, washed with 5% NaHCO₃ and brine, dried (MgSO₄) and evaporated to afford the desired ketone as a yellow liquid.

Step 2: 3-[2-(1-Isopropoxydimethylsilylbutan-2-ol)]toluene

A solution of the ketone from step 1 (2.5 g) in THF (15 mL) was added dropwise to a 0° C. solution of isopropoxydimethylsilylmethylmagnesium chloride (5.6 mmoL, J. Org. Chem., 1983, 48, 2120) in THF (10 mL). The mixture was stirred at r.t. under argon for 2 hr. before it was washed with saturated NH₄Cl solution and brine, dried (MgSO₄) and evaporated. Flash chromatography of the residue (silica gel; hexane/EtOAc (95:5)) yielded the title alcohol as a colorless oil.

Step 3: 3-[2-(Butan-1,2-diol)]toluene

A mixture of the alcohol from Step 2 (3.67 g), THF (20 mL), MeOH (20 mL), NaHCO₃ (1.25 g) and H₂O₂ (30%) (12.8 mL) was refluxed for 3 hr. After evaporation, the residue was taken up in EtOAc and the organic phase was washed with brine, dried (MgSO₄) and evaporated. Flash chromatography of the residue (silica gel; hexane/EtOAc (3:2)) yielded the desired diol as a colorless oil.

Step 4: 3-[4-(2,2-Dimethyl-4-ethyl-1,3-dioxalanyl)]toluene

Concentrated sulphuric acid (1 drop) was added to a solution of the diol from Step 3 (1.0 g) in acetone (50 mL). The reaction mixture was stirred for 2 hr. at r.t. before it was neutralized by the addition of 1N NaOH and evaporated. Flash chromatography of the residue (silica gel; hexane/EtOAc (75:5)) afforded the title toluene as a colorless oil.

Step 5: 3-[4-(2,2-Dimethyl-4-ethyl-1,3-dioxalanyl)]benzyl bromide

Following the procedure described in Halide 1, Step 3, but substituting the toluene from Step 4 for 3-[4-(4-methoxy)tetrahydropyranyl]toluene, the title benzyl bromide was obtained as an oil.

Halide 8: 3-[4-(4-Methoxy)tetrahydropyranyl]benzyl chloride

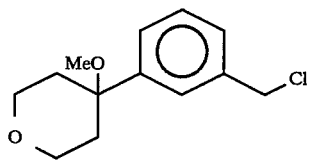

Following the procedure described for Halide 3, Steps 3–5, but substituting methyl iodide for ethyl iodide as starting material, the title compound was obtained as an oil.

PREPARATION OF ALCOHOLS

Alcohol 1: 3-[4-(4-Hydroxy)tetrahydropyranyl]benzyl alcohol

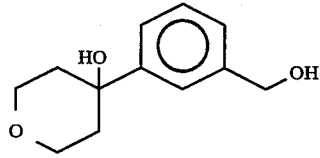

Step 1: 3-Bromo-O-tert-butyldiphenylsilylbenzyl alcohol

To a solution of 3-bromobenzyl alcohol (25 g, 134 mmoL) in anhydrous DMF (300 mL) was added triethylamine (17.6 g, 174 mmoL) followed by t-butyldiphenylsilyl chloride (40.4 g, 147 mmoL). The mixture was stirred for 24 hr, poured into a saturated aqueous NH₄Cl solution (1 L), and extracted with Et₂O. The combined organic layers were washed with brine, dried over MgSO₄ and evaporated. Flash chromatography on silica gel (2.5% EtOAc in hexane) afforded the title compound as a colorless oil.

Step 2: 3-[4-(4-Hydroxy)tetrahydropyranyl]benzyl alcohol

Following the procedure described in Halide 1, Step 1, but substituting 3-bromo-O-tert-butyldiphenylsilylbenzyl alcohol (from Step 1) for 3-bromotoluene, the tert-butyldiphenylsilylether derivative of the title compound was obtained. The crude product was treated with 5 equivalents of Bu₄NF in dry THF at r.t. for 1.5 hr. After evaporation of the solvent, the crude product was flash chromatographed on silica gel (toluene:EtOAc/1:4) to afford the pure title compound as a colorless oil.

Alcohols 2 and 3: 3-[4-(4α-Hydroxy-2-methyl)tetrahydropyranyl]benzyl alcohol (2) and 3-[4-(4β-hydroxy-2-methyl)tetrahydropyranyl]benzyl alcohol (3)

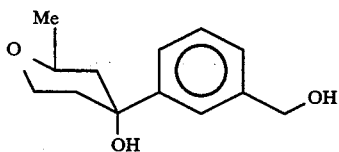

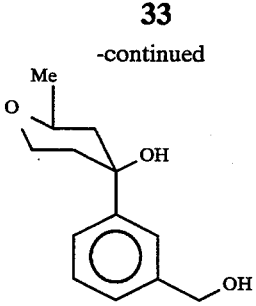

Following the procedure in Halide 1, Step 1, but substituting 3-bromo-O-tert-butyldiphenylsilylbenzyl alcohol (from Alcohol 1, Step 1) for 3-bromotoluene and substituting 2-methyltetrahydropyran-4-one (Jour. Amer. Chem. Soc., 1982, 104, 4666) for tetrahydropyran-4-one. The tert-butyldiphenylsilylether derivatives of the title compounds were obtained as a mixture of α- and β-isomers. This mixture was then treated with 5 equivalents of Bu₄NF in dry THF at r.t. for 1.5 hr. After evaporation of the solvent both isomers were separated by using flash chromatography (toluene:EtOAc/1:4) affording firstly the α-hydroxy isomer (Alcohol 2) followed by the β-isomer (Alcohol 3) in the ratio (1:2.8), respectively.

Alcohol 4: [1S,5R]3-[3-(3α-Hydroxy-6,8-dioxabicyclo[3.2.1]octanyl)]-benzyl alcohol

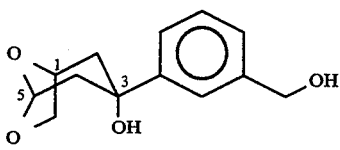

Step 1: 2,4-Di-O-p-toluenesulfonyl-1,6-anhydro-β-D-glucose

To a solution of 1,6-anhydro-13-β-glucose (50 g, 308 mmoL) in dry pyridine (100 mL) at 0° C. was added dropwise a solution of p-toluenesulfonyl chloride (123 g, 647 mmoL) dissolved in CHCl₃ (350 mL) and pyridine (200 mL). The reaction mixture was stirred at r.t. for at least 2 days. Water was added and the reaction mixture was stirred for ~1 hr, then the organic layer was decanted and the aqueous phase was reextracted with CHCl₃. The combined organic layers were washed with H₂SO₄ (10%) until the pH remained acidic, then finally washed with a saturated NH₄OAc-solution. The resulting organic layer was dried over MgSO₄ and the solvent evaporated. The syrup obtained was flash chromatographed on silica gel eluting with hexane:EtOAc (1:1) to give the title compound an oil.

Step 2: [1S,3S,5R]6,8-Dioxabicyclo[3.2.1]octan-3-ol

The ditosylate derivative from Step 1 (107 g, 0.228 mmoL) was dissolved in THF (1.6 L) at −40° C. and Super-hydride in THF (800 mL, 1M, 0.8 mmoL) was slowly added. The resulting reaction mixture was stirred at r.t. overnight. The reaction was cannulated into cold H₂O (226 mL) using external cooling, then NaOH 3N (640 mL, 1.92 mmol) and H₂O₂ (30%) (490 mL, 4.3 mmol) were successively added. The reaction was stirred at r.t. for 1 hr, then the supernatant (THF layer) was separated from the aqueous layer and concentrated. The resulting residue was combined with the aqueous layer and extracted with CH₂Cl₂ using a continuous extractor. The organic layer was dried (MgSO₄) and evaporated to dryness. The oily residue was dissolved in hot Et₂O, filtered and evaporated to dryness affording the title compound contaminated with the 2-octanol isomer. The crude product was used as such for the next step.

Step 3: [1S,5R]6,8-dioxabicyclo[3.2.1]octan-3-one

The crude alcohol from Step 2 (16.6 g, 89 mmoL) in CH₂Cl₂ (200 mL) was added slowly to a suspension of PCC (38.4 g, 178 mmoL) and celite (22 g) in CH₂Cl₂ (400 mL) and stirred for 1 hr. The reaction mixture was diluted with Et₂O (600 mL) and filtered over celite. The filtrate was evaporated and the residue distilled with a Kügelrohr apparatus (100° C., 1.8 mm/Hg) affording the title product as an oil.

Step 4: [1S,5R]3-[3-(3α-Hydroxy-6,8-dioxabicyclo[3,2,1]octanyl]-benzyl alcohol

Following the procedure described in Halide, Step 1, but substituting 3-bromo-O-tert-butyldiphenylsilylbenzyl alcohol (from Alcohol 1, Step 1) for 3-bromotoluene, the tert-butyldiphenylsilylether derivative of the title compound was obtained. The crude product was treated with 1 equivalent of Bu₄NF in dry THF at r.t. for 1.5 hr. After evaporation of the solvent, the crude product was flash chromatographed on silica gel (hexane:EtOAc/4:1) to afford the pure title product as a colorless oil.

Alcohol 5: 5-[4-(4-Hydroxy)tetrahydropyranyl]pyridin-3-ylmethanol

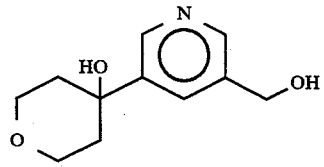

Step 1: 5-Bromo-O-tert-butyldiphenylsilylpyridin-3-ylmethanol

To a solution of 5-bromopyridin-3-ylmethanol (Chem. Pharm. Bull. 1990, 38, 2446) (29 g, 154 mmoL) and tert-butylchlorodiphenylsilane (47.5 g, 173 mmoL) in CH₂Cl₂ (500 mL) at r.t., there was added imidazole (15.8 g, 232 mmoL). The mixture was stirred for 1 hr. and filtered. The filtrate was evaporated and the residue chromatographed on silica gel eluting with a 1:7 mixture of EtOAc and hexane, to afford the product as a colorless oil.

Step 2: 5-[4-(4-Hydroxy)tetrahydropyranyl]-O-tert-butyldiphenylsilylpyridin-3-ylmethanol To a solution of the silylether from Step 1 (50 g, 117 mmoL) in THF (500 mL), cooled to −70° C., there was slowly added n-BuLi in hexanes (115 mL, 129 mmoL, 1.12M) affording a dark brown solution. To this, there was added a solution of tetrahydro-4H-pyran-4-one (14.1 g, 141 mmoL) in THF (925 mL). The resulting mixture was stirred for 1 hr. at −70° C., then quenched slowly with saturated aqueous NH₄Cl (50 mL) and allowed to warm to r.t. After diluting with EtOAc (500 mL) the mixture was washed (4×) with brine, dried over Na₂SO₄ and evaporated. Chromatography on silica gel, eluting with EtOAc, afforded the product as an oil which solidified.

Step 3: 5-[4-(4-Hydroxy)tetrahydropyranyl]pyridin-3-ylmethanol

To a solution of the silylether from Step 2 (20.35 g, 45.5 mmoL) in THF (350 mL), there was added Bu₄NF in THF (52 mL, 1M) and the mixture was stirred at r.t. for 1 hr. The solvent was evaporated and the residue chromatographed as a short column of silica gel, eluting with a 1:4 mixture of EtOH and EtOAc to afford the title product which was obtained, after trituration with Et₂O and filtration, as a light yellow solid, m.p. 145°–147° C.

Alcohol 6: 6-[4-(4-Hydroxy)tetrahydropyranyl]pyridin-2-ylmethanol

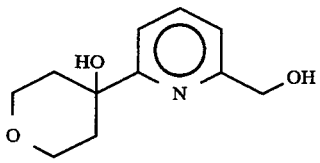

Step 1: 2-Bromo-6-[4-(4-hydroxy)tetrahydropyranyl]-pyridine

A solution of 2,6-dibromopyridine (15 g) in Et₂O (375 mL) was cooled to −78° C. To the resulting suspension was slowly added n-BuLi in hexanes (47.5 mL, 2M, 0.9 eq.) and the resulting mixture was stirred for a further 15 min. at −78° C. There was slowly added a solution of tetrahydro-4H-pyran-4-one (11.6 g) in Et₂O (25 mL). The resulting white suspension was stirred at −78° C. for an additional 15 min. There was added saturated aqueous NH₄Cl (100 mL) and the mixture was allowed to warm to r.t. After dilution with EtOAc, the organic phase was washed (4×) with brine, dried and evaporated. The residue was triturated with Et₂O and filtered to afford the title product as a white solid, m.p. 131°–133° C.

Step 2: 6-[4-(4-Hydroxy)tetrahydropyranyl]pyridin-2-ylmethanol

To a solution of the bromo derivative from Step 1 (7.7 g) in THF (50 mL) and Et₂O (150 mL), cooled to 0° C., there was slowly added n-BuLi in hexanes (30 mL, 2M) affording a red-brown suspension. An inlet tube above the surface of the mixture was connected to a flask in which paraformaldehyde (25 g) was gently heated at 175° C. to generate formaldehyde. When all the paraformaldehyde had been decomposed, to the reaction mixture was added saturated aqueous NH₄Cl (100 mL) and EtOAc (500 mL). The organic phase was washed (4×) with brine, dried and evaporated to a residue which was chromatographed on silica gel, eluting with EtOAc to afford the title product as a thick yellow oil.

Alcohol 7: 6-[4-(4-Methoxy)tetrahydropyranyl]pyridin-2-ylmethanol

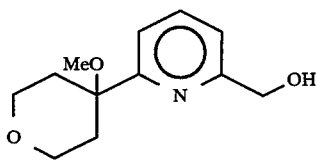

Step 1: 2-Bromo-6-[4-(4-methoxy)tetrahydropyranyl]-pyridine

To a suspension of KH (35% dispersion in oil, 1.25 g) in THF (75 mL), cooled to 0° C., there was added 2-bromo-6-[4-(4hydroxy)tetrahydropyranyl]pyridine from Alcohol 6, Step 1. When gassing had subsided, the mixture was warmed to r.t. and a thick suspension resulted. To this was added methyl iodide (1.71 g) and the resulting suspension was stirred at r.t. for 30 min. The THF was evaporated away, and the residue was partitioned between H₂O and EtOAc. The residue from evaporation of the organic phase was triturated with hexane and filtered to afford the product as a white solid, m.p. 69°–71° C.

Step 2: 6-[4-(4-Methoxy)tetrahydropyranyl]pyridin-2-ylmethanol

Following the procedure described in Alcohol 6, Step 2, but substituting the bromo derivative from Step 1 for 2-bromo-6-[4-(4-hydroxy)tetrahydropyranyl]pyridine, the title product was obtained as a white solid, m.p. 84°–86° C.

Alcohol 8: 4-[4-(4-Hydroxy)tetrahydropyranyl]pyridin-2-ylmethanol

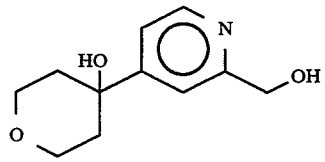

Following the procedure described in Alcohol 5, Steps 1–3, but substituting 4-bromopyridin-2-ylmethanol (Chem. Pharm. Bull. 1990, 38, 2446) for 5-bromo-pyridin-3-ylmethanol as starting material, the title product was obtained as a white solid.

Alcohol 9: [1S,5R]5-[3-(3α-Hydroxy-6,8-dioxabicyclo[3.2.1]-octanyl)]pyridin-3-ylmethanol

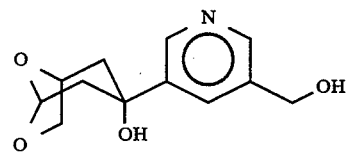

Following the procedure described in Alcohol 5, Steps 2–3, but substituting [1S,5R]6,8-dioxabicyclo[3.2.1]octan-4-one from Alcohol 4, Step 3, for tetrahydro-4H-pyran-4-one, the title product was obtained as a white solid.

Alcohol 10: [1S,5R]6-[3-(3α-Hydroxy-6,8-dioxabicyclo[3.2.1]-octanyl)]pyridin-2-ylmethanol

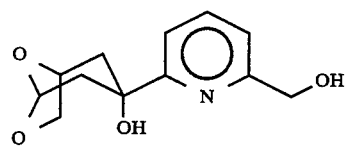

Step 1: 6-Bromo-O-tert-butyldiphenylsilylpyridin-2-ylmethanol

Following the procedure described in Alcohol 5, Step 1, but substituting 6-bromopyridin-2-ylmethanol (Chem. Pharm. Bull. 1990, 38, 2446) for 5-bromopyridin-3-ylmethanol, the title product was obtained as a colorless oil.

Step 2: [1S,5R]6-[3-(3α-Hydroxy-6,8-dioxabicyclo[3.2.1]-octanyl)]pyridin-2-ylmethanol Following the procedure described in Alcohol 5, Steps 2–3, but substituting 6-bromo-O-tert-butyldiphenyl-silylpyridin-2-ylmethanol from Step 1, for 5-bromo-O-tert-butyldiphenylsilylpyridin-3-ylmethanol and substituting [1S,5R]6,8-dioxabicyclo[3.2.1]octan-4-one from Alcohol 4, Step 3, for tetrahydro-4H-pyran-4-one, the title product was obtained as a white solid.

EXAMPLE 1

4-Phenyl-7-{3-[4-(4-methoxy)tetrahydropyranyl]benzyloxy}-2-quinolinone

Step 1: N-(3-Methoxyphenyl)benzoylacetamide

A solution of m-anisidine (10 g), ethyl benzoylacetate (19 g) and pyridine (2 drops) in xylene (20 mL) was heated to reflux for 5 hr. The mixture was cooled to r.t. and concentrated. The residual material was subjected to chromatography (silica gel; hexane/EtOAc (4:1)), affording the title compound as an oil.

Step 2: 7-Methoxy-4-phenyl-2-quinolinone

A mixture of N-(3-methoxyphenyl)benzoylacetamide (5.8 g), o-phosphoric acid (30 mL of 85% acid in $H_2O$) and $H_2O$ (30 mL) was heated at 100°–110° C. for 6 hr. After cooling to r.t., $H_2O$ (50 mL) was added and the precipitate that formed was collected by filtration. The title compound was thus obtained as a mixture with the regioisomeric product, 5-methoxy-4-phenyl-2-quinolinone, and used as such.

Step 3: 7-Hydroxy-4-phenyl-2-quinolinone

The quinolinone mixture prepared in Step 2 (1.5 g) and pyridine hydrochloride (3.75 g) were heated at 175°–180° C. for 10 hr. While still hot, $H_2O$ (50 mL) was added, causing the formation of a precipitate. Filtration and drying of this material provided the title compound as a solid as well as the regioisomeric 5-hydroxy-4-phenyl-2-quinolinone.

Step 4: 4-Phenyl-7-{3-[4-(4-methoxy)tetrahydropyranyl]-benzyloxy}-2-quinolinone

A mixture of 7-hydroxy-4-phenyl-2-quinolinone (827 mg), 3-[4-(4-methoxy)tetrahydropyranyl]benzyl chloride (Halide 8) (0.8 mL) and $K_2CO_3$ (963 mg) in DMF (10 mL) was stirred at 50°–60° C. After 6 hr, $H_2O$ (100 mL) was added and the aqueous phase extracted with EtOAc (3×). The organic phases were washed with $H_2O$ (2×) and brine before being dried ($MgSO_4$) and evaporated. The residue was subjected to flash chromatography (silica gel; EtOAc) and provided the title compound as a solid, m.p. 202°–203° C.

EXAMPLE 2

1-Methyl-4-phenyl-7-{3-[4-(4-hydroxy)tetrahydropyranyl]benzyloxy}-2-quinolinone

Step 1: 7-Methoxy-1-methyl-4-phenyl-2-quinolinone

A solution of 7-methoxy-4-phenyl-2-quinolinone from Example 1, Step 2 (1.62 g) in DMF (30 mL) was treated with NaH (60% in mineral oil; 310 mg). After stirring at 50° C. for 45 min., the mixture was cooled to r.t. and methyl iodide (0.6 mL) was added. After 30 min., $H_2O$ (100 mL) was added and the resulting solution extracted with EtOAc (3×). The organics were washed with $H_2O$ (2×), brine, dried ($MgSO_4$) and the solvents evaporated. Flash chromatography of the residue (silica gel; $CHCl_3$/EtOAc (4:1)) provided the title compound as a foam.

Step 2: 7-Hydroxy-1-methyl-4-phenyl-2-quinolinone

Following the procedures described in Example 1, Step 3, but substituting 7-methoxy-1-methyl-4-phenyl-2-quinolinone from Step 1 for 7-methoxy-4-phenyl-2-quinolinone, the title compound was obtained as a solid.

Step 3: 1-Methyl-4-phenyl-7-{3-[4-(4-hydroxy)tetrahydropyranyl]-benzyloxy}-2-quinolinone A mixture of 3-[4-(4-hydroxy)tetrahydropyranyl]benzyl bromide (Halide 2) (130 mg), the quinolinone from Step 2 (110 mg) and $K_2CO_3$ (121 mg) in DMF (2.5 mL) was stirred at r.t. for 15 hr. Water (50 mL) was added and the aqueous phase extracted with EtOAc. The organics were washed with $H_2O$, brine, dried ($MgSO_4$) and evaporated. Flash chromatography (silica gel; $CHCl_3$/EtOAc (2:1)) afforded the title compound as a colorless foam.

$^1H$ NMR (300 MHz, $CDCl_3$): δ1.70 (d, 2H), 1.79 (s, 1H), 2.21 (m, 2H), 3.72 (s, 3H), 3.87–4.00 (m, 4H), 5.19 (s, 1H), 6.54 (s, 1H), 6.83 (dd, 1H), 6.96 (d, 1H), 7.38–7.50 (m, 9H), 7.63 (s, 1H).

EXAMPLE 3

1-Methyl-4-phenyl-7-{3-[4-(4-methoxy)tetrahydropyranyl]benzyloxy}-2-quinolinone

Following the procedure described in Example 1, Step 4, but substituting 7-hydroxy-1-methyl-4-phenyl-2-quinolinone from Example 2, Step 2 for 7-hydroxy-4-phenyl-2-quinolinone, the title compound was obtained as a colorless foam.

$^1H$ NMR (300 MHz, $CDCl_3$): δ1.95–2.10 (m, 4H), 2.98 (s, 3H), 3.72 (s, 3H), 3.84–3.92 (m, 4H), 5.20 (s, 2H), 6.54 (s, 1H), 6.83 (dd, 1H), 6.96 (d, 1H), 7.37–7.51 (m, 10H).

EXAMPLE 4

1-Ethyl-4-phenyl-7-{3-[4-(4-methoxy)tetrahydropyranyl]benzyloxy}-2-quinolinone

Step 1: 1-Ethyl-7-hydroxy-4-phenyl-2-quinolinone

Following the procedures described in Example 2, Steps 1 and 2, but substituting ethyl iodide for methyl iodide, the title compound was obtained as a solid.

Step 2: 1-Ethyl-4-phenyl-7-{3-[4-(4-methoxy)tetrahydropyranyl]-benzyloxy}-2-quinolinone Following the procedure described in Example 1, Step 4, but substituting 1-ethyl-7-hydroxy-4-phenyl-2-quinolinone for 7-hydroxy-4-phenyl-2-quinolinone, the title compound was obtained as a white solid, m.p. 155°–156° C.

EXAMPLE 5

1-Benzyl-4-phenyl-7-{3-[4-(4-hydroxy)tetrahydropyranyl]benzyloxy}-2-quinolinone

Following the procedures described in Example 2, but substituting benzyl bromide for methyl iodide, the title compound was obtained as a white solid, m.p. 179°–180° C.

EXAMPLE 6

1-Benzyl-4-phenyl-7-{3-[4-(4-methoxy)tetrahydropyranyl]benzyloxy}-2-quinolinone

Following the procedure described in Example 4, but substituting benzyl bromide for ethyl iodide, the title compound was obtained as a white solid, m.p. 136°–138° C.

EXAMPLE 7

1-(2-Picolyl)-4-phenyl-7-{3-[4-(4-methoxy)tetrahydropyranyl]benzyloxy}-2-quinolinone Following the procedure described in Example 2, Step 1, but substituting 2-picolyl chloride hydrochloride for methyl iodide and the quinolinone of Example 1, Step 4, for 7-methoxy-4-phenyl-2-quinolinone, the title compound was obtained as a colorless foam.

$^1H$ NMR (300 MHz, $CDCl_3$): δ1.95–2.10 (m, 4H), 2.97 (s, 3H), 3.80–3.89 (m, 4H), 5.06 (s, 2H), 5.69 (s, 2H), 6.62 (s, 1H), 6.78 (dd, 1H), 7.18–7.50 (m, 13H), 7.62 (dt, 1H), 8.60 (m, 1H).

EXAMPLE 8

1-(4-Cyano)benzyl-4-phenyl-7-{3-[4-(4-methoxy)tetrahydropyranyl]benzyloxy}-2-quinolinone Following the procedures described in Example 7, but substituting 4-cyanobenzyl bromide for 2-picolyl chloride hydrochloride, the title compound was obtained as a white solid, m.p. 161°–162° C.

EXAMPLE 9

1-[4-(2-Methyl)thiazolylmethyl]-4-phenyl-7-{3-[4-(4-methoxy)tetrahydropyranyl]benzyloxy}-2-quinolinone Following the procedures described in Example 7, but substituting 4-chloromethyl-2-methylthiazole hydrochloride for 2-picolyl chloride hydrochloride, the title compound was obtained as a colorless foam.

$^1$H NMR (300 MHz, CDCl$_3$): $\delta$1.94–2.10 (m, 4H), 2.73 (s, 3H), 2.97 (s, 3H), 3.79–3.92 (m, 4H), 5.15 (s, 2H), 5.61 (s, 2H), 6.58 (s, 1H), 6.80 (dd, 1H), 7.00 (s, 1H), 7.34–7.51 (m, 11H).

EXAMPLE 10

1-Cyclohexylmethyl-4-phenyl-7-{3-[4-(4-methoxy)tetrahydropyranyl]benzyloxy}-2-quinolinone Following the procedures described in Example 7, but substituting cyclohexylmethyl bromide for 2-picolyl chloride hydrochloride, the title compound was obtained as a white solid, m.p. 120°–121° C.

EXAMPLE 11

1-(1-Naphthylmethyl)-4-phenyl-7-{3-[4-(4-methoxy)tetrahydropyranyl]benzyloxy}-2-quinolinone Following the procedures described in Example 4, but substituting (1-chloromethyl)naphthalene for ethyl iodide, the title compound was obtained as a white solid, m.p. 183°–185° C.

EXAMPLE 12

1-(3-Picolyl)-4-phenyl-7-{3-[4-(4-methoxy)tetrahydropyranyl]benzyloxy}-2-quinolinone Following the procedures described in Example 4, but substituting 3-picolyl chloride hydrochloride for ethyl iodide, the title compound was obtained as a white solid, m.p. 116°–118° C.

EXAMPLE 13

1-(3-Carbomethoxy)benzyl-4-phenyl-7-{3-[4-(4-methoxy)tetrahydropyranyl]benzyloxy}-2-quinolinone Following the procedures described in Example 7, but substituting methyl 3-bromomethylbenzoate for 2-picolyl chloride hydrochloride, the title compound was obtained as a white solid, m.p. 157°–159° C.

EXAMPLE 14

1,4-Diphenyl-7-{3-[4-(4-methoxy)tetrahydropyranyl]benzyloxy}-2-quinolinone

Step 1: 1,4-Diphenyl-7-methoxy-2-quinolinone

A mixture of the quinolinone of Example 1, Step 2 (151 mg), K$_2$CO$_3$ (141 mg), CuBr (103 mg) in iodobenzene (2 mL), and pyridine (1 mL) was heated at reflux for 4.5 hr. The mixture was cooled to r.t. and EtOAc (50 mL) and 1N HCl (50 mL) were added. The organics were separated and the aqueous was extracted with EtOAc (3×). The combined organics were washed with 1N HCl, brine, dried (MgSO$_4$) and evaporated. Flash chromatography of the residue (silica gel; hexane/EtOAc (3:2)) provided the title compound as a white solid.

Step 2: 1,4-Diphenyl-7-{3-[4-(4-methoxy)tetrahydropyranyl]-benzyloxy}-2-quinolinone Following the procedure described in Example 1, Steps 3 and 4, but substituting 1,4-diphenyl-7-methoxy-2-quinolinone for 7-methoxy-4-phenyl-2-quinolinone, the title compound was obtained as a white solid, m.p. 142°–144° C.

EXAMPLE 15

1-Benzyl-4-(3-furyl)-7-{3-[4-(4-hydroxy)tetrahydropyranyl]benzyloxy}-2-quinolinone Step 1: 4-(3-Furyl)-7-methoxy-2-quinolinone Following the procedures described in Example 1, Steps 1 and 2, but substituting ethyl $\beta$-oxo-3-furanpropionate for ethyl benzoylacetate, the title compound was obtained as a beige solid.

Step 2: 1-Benzyl-4-(3-furyl)-7-hydroxy-2-quinolinone

Following the procedures described in Example 2, Steps 1 and 2, but substituting 4-(3-furyl)-7-methoxy-2-quinolinone for 7-methoxy-4-phenyl-2-quinolinone and benzyl bromide for methyl iodide, the title compound was obtained as a solid.

Step 3: 1-Benzyl-4-(3-furyl)-7-{3-[4-(4-hydroxy)tetrahydropyranyl]benzyloxy}-2-quinolinone Following the procedure described in Example 2, Step 3, but substituting 1-benzyl-4-(3-furyl)-7-hydroxy-2-quinolinone for 7-hydroxy-1-methyl-4-phenyl-2-quinolinone, the title compound was obtained as a solid, m.p. 171°–172° C.

EXAMPLE 16

1-Benzyl-4-(3-furyl)-7-{3-[4-(4-methoxy)tetrahydropyranyl]benzyloxy}-2-quinolinone Following the procedure described in Example 1, Step 4, but substituting 1-benzyl-4-(3-furyl)-7-hydroxy-2-quinolinone for 7-hydroxy-4-phenyl-2-quinolinone, the title compound was obtained as a solid, m.p. 132°–133° C.

EXAMPLE 17

1-(4-Chloro)benzyl-4-(3-furyl)-7-{3-[4-(4-methoxy)tetrahydropyranyl]benzyloxy}-2-quinolinone Step 1: 1-(4-Chloro)benzyl-4-(3-furyl)-7-hydroxy-2-quinolinone Following the procedure described in Example 15, Step 2, but substituting 4-chlorobenzyl bromide for benzyl bromide, the title compound was obtained as a solid.

Step 2: 1-(4-Chloro)benzyl-4-(3-furyl)-7-{3-[4-(4-methoxy)tetrahydropyranyl]benzyloxy}-2-quinolinone Following the procedures described in Example 1, Step 4, but substituting 1-(4-chloro)benzyl-4-(3-furyl)-7-hydroxy-2-quinolinone for 7-hydroxy-4-phenyl-2-quinolinone, the title compound was obtained as a white solid, m.p. 155°–156° C.

EXAMPLE 18

[1S,5R]1-Benzyl-4-(3-furyl)-7-{[1S,5R]3-[3-(3$\alpha$-hydroxy-6,8-dioxabicyclo[3.2.1]octanyl)]benzyloxy}-2-quinolinone A mixture of 1-benzyl-4-(3-furyl)-7-hydroxy-2-quinolinone (101 mg), Alcohol 4 (75 mg), triphenylphosphine (150 mg) and di-t-butylazodicarboxylate (95 mg) in THF (7 mL) was stirred at r.t. for 15 hr. The solution was concentrated and the residue subjected to flash chromatography (silica gel; EtOAc/hexane (2:1)) to provide the title compound as a white solid, m.p. 78°–80° C.

EXAMPLE 19

1-Benzyl-4-(3-furyl)-7-{5-[4-(4-hydroxy)tetrahydropyranyl]pyridin-3-ylmethoxy}-2-quinolinone Following the procedure described in Example 18, but substituting Alcohol 5 for Alcohol 4, the title compound was obtained as a solid, m.p. 205°–208° C.

EXAMPLE 20

1-(4-Fluoro)benzyl-4-(3-furyl)-7-{5-[4-(4-hydroxy)tetrahydropyranyl]pyridin-3-ylmethoxy}-2-quinolinone Step 1: 1-(4-Fluoro)benzyl-4-(3-furyl)-7-hydroxy-2-quinolinone Following the procedures described in Example 15, Step 2, but substituting 4-fluorobenzyl bromide for benzyl bromide, the title compound was obtained as a solid.

Step 2: 1-(4-Fluoro)benzyl-4-(3-furyl)-7-{5-[4-(4-hydroxy)tetrahydropyranyl]pyridin-3-ylmethoxy-2-quinolinone Following the procedures described in Example 19, but substituting 1-(4-fluoro)benzyl-4-(3-furyl)-7-hydroxy-2-quinolinone for 1-benzyl-4-(3-furyl)-7-hydroxy-2-quinolinone, the title compound was obtained as a solid, m.p. 207°–210° C.

EXAMPLE 21

1-(4-Fluoro)benzyl-4-(3-furyl)-7-{6-[4-(4-hydroxy)tetrahydropyranyl]pyridin-2-ylmethoxy-2-quinolinone A mixture of 1-(4-fluoro)benzyl-4-(3-furyl)-7-hydroxy-2-quinolinone (1.03 mg), Alcohol 6 (71 mg), triphenylphosphine (145 mg) and di-t-butylazodicarboxylate (92 mg) in THF (7 mL) was stirred at r.t. for 15 hr. The solution was concentrated and the residue subjected to flash chromatography (silica gel; EtOAc/ethanol (50:1)) to provide the title compound as a solid, m.p. 169°–171° C.

EXAMPLE 22

1-(4-Chloro)benzyl-4-(3-furyl)-7-{6-[4-(4-hydroxy)tetrahydropyranyl]pyridin-2-ylmethoxy-2-quinolinone Following the procedures described in Example 21, but substituting 1-(4-chloro)benzyl-4-(3-furyl)-7-hydroxy-2-quinolinone (Example 17, Step 1) for 1-(4-fluoro)benzyl-4-(3-furyl)-7-hydroxy-2-quinolinone, the title compound was obtained as a solid, m.p. 155°–157° C.

EXAMPLE 23

[1S,5R]1-Benzyl-4-(3-furyl)-7-{6-[3-(3α-hydroxy-6,8-dioxabicyclo[3.2.1]octanyl)]pyridin-2-ylmethoxy-2-quinolinone Following the procedures described in Example 18, but substituting Alcohol 10 for Alcohol 4, the title compound was obtained as a solid, m.p. 154°–156° C.

EXAMPLE 24

1-Benzyl-4-(3-thienyl)-7-{3-[4-(4-hydroxy)tetrahydropyranyl]benzyloxy}-2-quinolinone Step 1: 7-Methoxy-4-(3-thienyl)-2-quinolinone Following the procedures described in Example 1, Steps 1 and 2, but substituting ethyl β-oxo-3-thiophenepropionate for ethyl benzoylacetate, the title compound was obtained as a solid.

Step 2: 1-Benzyl-7-hydroxy-4-(3-thienyl)-2-quinolinone

Following the procedures described in Example 2, Steps 1 and 2, but substituting 7-methoxy-4-(3-thienyl)-2-quinolinone for 7-methoxy-4-phenyl-2-quinolinone and benzyl bromide for methyl iodide, the title compound was obtained as a solid.

Step 3: 1-Benzyl-4-(3-thienyl)-7-{3-[4-(4-hydroxy)tetrahydropyranyl]benzyloxy}-2-quinolinone Following the procedure described in Example 2, Step 3, but substituting 1-benzyl-7-hydroxy-4-(3-thienyl)-2-quinolinone for 7-hydroxy-1-methyl-4-phenyl-2-quinolinone, the title compound was obtained as a solid, m.p. 177°–180° C.

EXAMPLE 25

1-Benzyl-4-(3-thienyl)-7-{3-[4-(4-methoxy)tetrahydropyranyl]benzyloxy}-2-quinolinone Following the procedures described in Example 1, but substituting 1-benzyl-7-hydroxy-4-(3-thienyl)-2-quinolinone for 7-hydroxy-4-phenyl-2-quinolinone, the title compound was obtained as a colorless foam.

$^1$H NMR (300 MHz, CDCl$_3$: δ1.91–2.07 (m, 4H), 2.95 (s, 3H), 3.80–3.90 (m, 4H), 4.99 (s, 2H), 5.53 (s, 2H), 6.68 (s, 1H), 6.80 (dd, 1H), 6.85 (d, 1H), 7.22–7.41 (m, 10H), 7.47 (m, 2H), 7.65 (d, 1H).

EXAMPLE 26

1-(3-Carbomethoxy)benzyl-4-(3-thienyl)-7-{3-[4-(4-methoxy)tetrahydropyranyl]benzyloxy}-2-quinolinone Step 1: 4-(3-Thienyl)-7-{3-[4-(4-methoxy)tetrahydropyranyl]benzyloxy}-2-quinolinone Following the procedures described in Example 1, Steps 3 and 4, but substituting 7-methoxy-4-(3-thienyl)-2-quinolinone from Example 24, Step 1 for 7-methoxy-4-phenyl-2-quinolinone, the title compound was obtained as a solid.

Step 2: 1-(3-Carbomethoxy)benzyl-4-(3-thienyl)-7-{3-[4-(4-methoxy)tetrahydropyranyl]benzyloxy}-2-quinolinone Following the procedure described in Example 2, Step 1, but substituting methyl 3-bromomethylbenzoate for methyl iodide and the quinolinone from Example 26, Step 1, for 7-methoxy-4-phenyl-2-quinolinone, the title compound was obtained as a white solid, m.p. 188°–189° C.

EXAMPLE 27

1-(4-Carbomethoxy)benzyl-4-(3-thienyl)-7-{3-[4-methoxy)tetrahydropyranyl]benzyloxy}-2-quinolinone Following the procedure described in Example 26, Step 2, but substituting methyl 4-bromomethylbenzoate for methyl 3-bromomethylbenzoate, the title compound was obtained as a light yellow solid, m.p. 138°–140° C.

EXAMPLE 28

3-[2-(2-Hydroxy)isopropyl]benzyl-4-(3-thienyl)-7-{3-[4-(4-methoxy)tetrahyropyranyl]benzyloxy}-2-quinolinone Following the procedure described in Example 26, Step 2, but substituting 3-[2-(2-hydroxy)isopropyl]benzyl mesylate for methyl 3-bromomethylbenzoate, the title compound was obtained as a colorless foam.

$^1$H NMR (300 MHz, CDCl$_3$): δ1.56 (s, 6H), 1.92–2.16 (m, 5H), 2.95 (s, 3H), 3.79–3.91 (m, 4H), 5.01 (s, 2H), 5.54 (brs, 2H), 6.67 (s, 1H), 6.80 (dd, 1H), 6.91 (d, 1H), 7.08 (brd, 1H), 7.24–7.46 (m, 7H), 7.46–7.49 (m, 2H), 7.56 (brs, 1H), 7.65 (d, 1H).

EXAMPLE 29

1-(3-Carboxy)benzyl-4-(3-thienyl)-7-{3-[4-(4-methoxy)-tetrahydropyranyl]benzyloxy}-2-quinolinone A mixture of the quinolinone of Example 26 (91 mg) and 1N LiOH (306 μL) in THF (6 mL) and MeOH (1 mL) was heated at 50° C. for 16 hr. To the mixture was added NH4OAc buffer and the resulting mixture was extracted with EtOAc (3×). The combined organics were washed with buffer, brine, dried (Na2SO4) and evaporated. Flash chromatography of the residue (silica gel; acetone/CHCl3/HOAc (50:50:1)) provided the title compound as a white solid, m.p. 223°–233° C. (dec.).

EXAMPLE 30

1-[1-(4-Hydroxy-4-methyl)pentyl]-4-(3-thienyl)-7-{3-[4-(4-methoxy)tetrahydropyranyl}benzyloxy}-2-quinolinone Step 1: 1-[1-(4-Acetoxy-4-methyl)pentyl]-4-(3-thienyl)-7-{3-[4-(4-methoxy)tetrahydropyranyl}benzyloxy}-2-quinolinone Following the procedures described in Example 26, Step 2, but substituting 4-acetoxy-4-methyl-O-tosylpentanol for methyl 3-bromomethylbenzoate, the title compound was obtained as a foam.

Step 2: 1-[1-(4-Hydroxy-4-methyl)pentyl]-4-(3-thienyl)-7-{3-[4-(4-methoxy)tetrahydropyranyl}benzyloxy}-2-quinolinone A mixture of the acetate from Step 1 (49 mg) and 1N LiOH (166 μL) in THF (2 mL) and MeOH (0.8 mL) was stirred at r.t. for 60 hr. NH4OAc buffer was added and the mixture extracted with EtOAc (3×). The combined organics were washed with buffer, brine, dried (MgSO4) and evaporated. Flash chromatography of the residue (silica gel; EtOAc/hexane/MeOH (50:45:5)) provided the title compound as a colorless foam.

$^1$H NMR (300 MHz, CDCl3): δ1.26 (s, 6H), 1.55–1.70 (m, 3H), 1.80–2.10 (m, 6H), 2.97 (s, 3H), 3.78–3.95 (m, 4H), 4.33 (t, 2H), 5.20 (s, 2H), 6.58 (s, 1H), 6.86 (dd, 1H), 7.00 (d, 1H), 7.21 (d, 1H), 7.36–7.52 (m, 6H), 7.68 (d, 1H).

EXAMPLE 31

1-Benzyl-4-(3-thienyl)-7-{5-[4-(4-hydroxy)tetrahydropyranyl]pyridin-3-ylmethoxy-2-quinolinone Following the procedures described in Example 19, but substituting 1-benzyl-7-hydroxy-4-(3-thienyl)-2-quinolinone (Example 24, Step 2) for 1-benzyl-7-hydroxy-4-(3-furyl)-2-quinolinone, the title compound was obtained as a white solid, m.p. 201°–203° C.

EXAMPLE 32

1-Benzyl-4-(3-thienyl)-7-{6-[4-(4-hydroxy)tetrahydropyranyl]pyridin-2-ylmethoxy}-2-quinolinone Following the procedures described in Example 21, but substituting 1-benzyl-7-hydroxy-4-(3-thienyl)-2-quinolinone (Example 24, Step 2) for 1-(4-fluoro)benzyl-7-hydroxy-4-(3-furyl)-2-quinolinone, the title compound was obtained as a colorless foam.

$^1$H NMR (300 MHz, CDCl3): δ1.53 (br t, 2H), 2.15 (dt, 2H), 3.92–4.06 (m, 4H), 5.14 (s, 2H), 5.52 (br s, 2H), 6.68 (s, 1H), 6.81 (dd, 1H), 6.86 (d, 1H), 7.22–7.34 (m, 8H), 7.48 (m, 2H), 7.65 (d, 1H), 7.73 (t, 1H).

EXAMPLE 33

1-Benzyl-4-methyl-7-{3-[4-(4-methoxy)tetrahydropyranyl]benzyloxy}-2-quinolinone

Step 1: 7-Methoxy-4-methyl-2-quinolinone

Following the procedures described in Example 1, Steps 1 and 2, but substituting methyl acetoacetate for ethyl benzoylacetate, the title compound was obtained as a solid.

Step 2: 1-Benzyl-7-hydroxy-4-methyl-2-quinolinone

Following the procedure described in Example 15, Step 2, but substituting 7-methoxy-4-methyl-2-quinolinone for 4-(3-furyl)-7-methoxy-2-quinolinone, the title compound was obtained as a solid.

Step 3: 1-Benzyl-4-methyl-7-{3-[4-(4-methoxy)tetrahydropyranyl]benzyloxy}-2-quinolinone Following the procedure described in Example 2, Step 3, but substituting 1-benzyl-7-hydroxy-4-methyl-2-quinolinone for 7-hydroxy-1-methyl-4-phenyl-2-quinolinone, the title compound was obtained as a white solid, m.p. 132°–134° C.

EXAMPLE 34

1-Benzyl-4-methyl-7-{5-[4-(4-hydroxy)tetrahydropyranyl]pyridin-3-ylmethoxy}-2-quinolinone Following the procedures described in Example 19, but substituting 1-benzyl-7-hydroxy-4-methyl-2-quinolinone (Example 33, Step 2) for 1-benzyl-4-(3-furyl)-7-hydroxy-2-quinolinone, the title compound was obtained as a white solid, m.p. 204°–205° C.

EXAMPLE 35

1-Benzyl-7-{3-[4-(4-methoxy)tetrahydropyranyl]benzyloxy}-2-quinolinone

Step 1: 7-Hydroxy-2-quinolinone

To a solution of 3-aminophenol (1 g) in CH2Cl2 (25 mL) and pyridine (1 mL) at 5° C. was added dropwise a solution of cinnamoyl chloride (1.53 g) in CH2Cl2 (10 mL). The mixture was warmed to r.t. over 1 hr, and then EtOAc (150 mL) was added. The organics were washed with H2O, 1N, HCl, saturated aq. NaHCO3 and H2O, dried (MgSO4) and concentrated. To the residue was added AlCl3 (6.38 g) and the mixture heated at 180° C. for 5 min. and then at 115°–120° C. for 2 hr. To the mixture was added ice and then H2O. The solid that formed was collected by filtration, washed with 2N HCl and H2O (3×). The resulting solid was triturated in EtOAc to provide the title compound.

Step 2: 7-{3-[4-(4-Methoxy)tetrahydropyranyl]benzyloxy}-2-quinolinone

Following the procedure described in Example 1, Step 4, but substituting 7-hydroxy-2-quinolinone for 7-hydroxy-4-phenyl-2-quinolinone, provided the title compound as a solid.

Step 3: 1-Benzyl-7-{3-[4-(4-methoxy)tetrahydropyranyl]benzyloxy}-2-quinolinone

Following the procedure described in Example 2, Step 1, but substituting 7-{3-[4-(4-methoxy)tetrahydropyranyl]benzyloxy}-2-quinolinone for 7-methoxy-4-phenyl-2-quinolinone and benzyl bromide for methyl iodide, the title compound was obtained as a white foam.

$^1$H NMR (300 MHz, CDCl3): δ1.92–2.07 (m, 4H), 2.95 (s, 3H), 3.80–3.91 (m, 4H), 4.99 (s, 2H), 5.49 (br s, 2H), 6.65 (d, 1H), 6.79 (d, 1H), 6.85 (dd, 1H), 7.20–7.42 (m, 9H), 7.47 (d, 1H), 7.67 (d, 1H).

EXAMPLE 36

1-Methyl-6-{3-[4-(4-methoxy)tetrahydropyranyl]benzyloxy}-2-quinolinone

Step 1: 6-Methoxy-2-quinolinone

To a solution of 6-methoxyquinoline (2.08 g) in CHCl3 (45 mL) at r.t. was added m-chloroperoxybenzoic acid (3.38 g) portionwise over 10 min. After 30 min., CHCl3 (50 mL) was added and the solution washed with saturated aq. NaHCO3 (3×), dried (MgSO4) and concentrated. A portion of this material (500 mg) in DMF (10 mL) was treated with trifluoroacetic anhydride (TFAA) and stirred at r.t. for 17 hr. The TFAA was removed under vacuum and to the resulting solution was added water (60 mL). The mixture was extracted with EtOAc (6×) and the combined organics were dried (MgSO$_4$) and concentrated. Trituration of the resulting material with acetone provided the title compound as a pale yellow solid.

Step 2: 6-Methoxy-1-methyl-2-quinolinone

Following the procedure described in Example 2, Step 1, but substituting 6-methoxy-2-quinolinone for 7-methoxy-4-phenyl-2-quinolinone, the title compound was obtained as a white solid.

Step 3: 6-Hydroxy-1-methyl-2-quinolinone

Following the procedure described in Example 1, Step 3, but substituting 6-methoxy-1-methyl-2-quinolinone for 7-methoxy-4-phenyl-2-quinolinone, the title compound was obtained as a solid.

Step 4: 1-Methyl-6-{3-[4-(4-methoxy)tetrahydropyranyl]benzyloxy}-2-quinolinone

Following the procedure described in Example 1, Step 4, but substituting 6-hydroxy-1-methyl-2-quinolinone for 7-hydroxy-4-phenyl-2-quinolinone, the title compound was obtained as a white foam.

$^1$H NMR (300 MHz, CDCl$_3$): δ1.95–2.11 (m, 4H), 2.98 (s, 3H), 3.71 (s, 3H), 3.80–3.92 (m, 4H), 5.13 (s, 2H), 6.72 (d, 1H), 7.09 (d, 1H), 7.25–7.49 (m, 6H), 7.59 (d, 1H).

EXAMPLE 37

1-Benzyl-6-{3-[4-(4-hydroxy)tetrahydropyranyl]benzyloxy}-2-quinolinone

Step 1: 1-Benzyl-6-hydroxy-2-quinolinone

Following the procedure described in Example 36, Steps 2 and 3, but substituting benzyl bromide for methyl iodide, the title compound was obtained as a solid.

Step 2: 1-Benzyl-6-{3-[4-(4-hydroxy)tetrahydropyranyl]benzyloxy}-2-quinolinone

Following the procedure described in Example 2, Step 3, but substituting 1-benzyl-6-hydroxy-2-quinolinone for 7-hydroxy-1-methyl-4-phenyl-2-quinolinone, the title compound was obtained as a white foam.

$^1$H NMR (300 MHz, CDCl$_3$): δ1.62–1.71 (m, 2H), 1.93 (s, 1H), 2.19 (dt, 2H), 3.80–3.98 (m, 4H), 5.08 (s, 2H), 5.54 (br s, 2H), 6.82 (d, 1H), 7.09–7.48 (m, 11H), 7.58 (s, 1H), 7.66 (d, 1H).

EXAMPLE 38

1-Benzyl-6-{3-[4-(4-methoxy)tetrahydropyranyl]benzyloxy}-2-quinolinone

Following the procedure described in Example 1, Step 4, but substituting 1-benzyl-6-hydroxy-2-quinolinone for 7-hydroxy-4-phenyl-2-quinolinone, the title compound was obtained as a white foam.

$^1$H NMR (300 MHz, CDCl$_3$): δ1.92–2.10 (m, 4H), 2.95 (s, 3H), 3.82–3.91 (m, 4H), 5.09 (s, 2H), 5.55 (br s, 2H), 6.81 (d, 1H), 7.09–7.44 (m, 12H), 7.66 (d, 1H).

EXAMPLE 39

1-Phenyl-6-{3-[4-(4-hydroxy)tetrahydropyranyl]benzyloxy}-2-quinolinone

Step 1: 6-Methoxy-1-phenyl-2-quinolinone

Following the procedure described in Example 14, Step 1, but substituting 6-methoxy-2-quinolinone for 7-methoxy-4-phenyl-2-quinolinone, provided the title compound as a solid.

Step 2: 6-Hydroxy-1-phenyl-2-quinolinone

Following the procedure described in Example 1, Step 3, but substituting 6-methoxy-1-phenyl-2-quinolinone for 7-methoxy-4-phenyl-2-quinolinone, the title compound was obtained as a solid.

Step 3: 1-Phenyl-6-{3-[4-(4-hydroxy)tetrahydropyranyl]benzyloxy}-2-quinolinone

Following the procedure described in Example 2, Step 3, but substituting 6-hydroxy-1-phenyl-2-quinolinone for 7-hydroxy-1-methyl-4-phenyl-2-quinolinone, the title compound was obtained as a colorless foam.

$^1$H NMR (300 MHz, CDCl$_3$): δ1.58–1.71 (m, 3H), 2.19 (dt, 2H), 3.85–3.99 (m, 4H), 5.10 (s, 2H), 6.59 (d, 1H), 6.79 (3, 1H), 7.02 (dd, 1H), 7.11 (d, 1H), 7.26–7.62 (m, 7H), 7.71 (d, 1H).

EXAMPLE 40

1-Phenyl-6-{3-[4-(4-methoxy)tetrahydropyranyl]benzyloxy}-2-quinolinone

Following the procedure described in Example 1, Step 4, but substituting 6-hydroxy-1-phenyl-2-quinolinone for 7-hydroxy-4-phenyl-2-quinolinone, the title compound was obtained as a white foam.

$^1$H NMR (300 MHz, CDCl$_3$): δ1.95–2.10 (m, 4H), 2.97 (s, 3H), 3.80–3.92 (m, 4H), 5.11 (s, 2H), 6.58 (d, 1H), 6.79 (d, 1H), 7.02 (dd, 1H), 7.11 (d, 1H), 7.26–7.60 (m, 9H), 7.70 (d, 1H).

EXAMPLE 41

2-Methoxy-4-phenyl-7-{3-[4-(4-methoxy)tetrahydropyranyl]benzyloxy}quinoline

A mixture of 4-phenyl-7-{3-[4-(4-methoxy)tetrahydropyranyl]benzyloxy}-2-quinolinone (51 mg), silver carbonate (32 mg) and methyl iodide (30 μL) in benzene (5 mL) was stirred at 40° C. for 24 hr and then filtered through celite, washing with EtOAc. The filtrate was concentrated and the residue subjected to flash chromatography (silica gel; hexane/EtOAc (3:1)) to provide the title compound as a colorless foam.

$^1$H NMR (300 MHz, CDCl$_3$): δ1.96–2.12 (m, 4H), 2.99 (s, 3H), 3.80–3.92 (m, 4H), 4.08 (s, 3H), 5.22 (s, 2H), 6.72 (s, 1H), 7.05 (dd, 1H), 7.35–7.53 (m, 10H), 7.65 (d, 1H).

EXAMPLE 42

2-Benzyloxy-4-phenyl-7-{3-[4-(4-methoxy)tetrahydropyranyl]benzyloxy}quinoline

Following the procedure described in Example 41, but substituting benzyl bromide for methyl iodide, the title compound was obtained as a colorless foam.

$^1$H NMR (300 MHz, CDCl$_3$): δ1.92–2.13 (m, 4H), 3.00 (s, 3H), 3.78–3.92 (m, 4H), 5.22 (s, 2H), 5.58 (s, 2H), 6.80 (s, 1H), 7.06 (dd, 1H), 7.30–7.55 (m, 15H), 7.68 (d, 1H).

EXAMPLE 43

2-(4-Cyano)benzyloxy-4-phenyl-7-{3-[4-(4-methoxy)tetrahydropyranyl]benzyloxy}quinoline Following the procedure described in Example 41, but substituting 4-cyanobenzyl bromide for methyl iodide, the title compound was obtained as a colorless foam.

$^1$H NMR (300 MHz, CDCl$_3$): δ1.96–2.12 (m, 4H), 2.99 (s, 3H), 3.80–3.93 (m, 4H), 5.22 (s, 2H), 5.63 (s, 2H), 6.82 (s, 1H), 7.08 (dd, 1H), 7.36–7.52 (m, 11H), 7.61–7.71 (m, 4H).

EXAMPLE 44

[1S,5R]4-Phenyl-7-{6-[3-(3α-hydroxy-6,8-dioxabicyclo[3.2.1]octanyl)]pyridin-2-ylmethoxy}quinoline
Step 1: 7-Methoxy-4-phenylquinoline To a solution of 7-methoxy-4-phenyl-2-quinolinone (4.1 g) in THF (300 mL) at reflux was added lithium aluminum hydride (1M in THF; 65 mL). The mixture was refluxed for 50 hr, cooled to 0° C. and then treated successively with H₂O (2.5 mL), 15% aq. NaOH (2.5 mL) and H₂O (7.5 mL). The precipitate that formed was removed by filtration, washed with THF, and the filtrate was concentrated and redissolved in acetonitrile (100 mL). To this solution at r.t. was added dropwise a solution of ceric ammonium nitrate (7.7 g) in H₂O (30 mL). After the addition was complete, H₂O (600 mL) was added and the resulting mixture extracted with EtOAc (3×). The combined organics were washed with H₂O (2×) and brine, dried (MgSO₄) and concentrated. Flash chromatography of the residue (silica gel; EtOAc/hexane (1:1)) provided the title compound as a beige gum.

Step 2: 7-Hydroxy-4-phenylquinoline

Following the procedure described in Example 1, Step 3, but substituting 7-methoxy-4-phenylquinoline for 7-methoxy4-phenyl-2-quinolinone, the title compound was obtained as a brown solid.

Step 3: [1S,5R]4-Phenyl-7-{6-[3-(3α-hydroxy-6,8-dioxabicyclo[3.2.1]octanyl)pyridin-2-ylmethoxy-quinoline Following the procedures described in Example 18, but substituting 7-hydroxy-4-phenylquinoline for 1-benzyl-4-(3-furyl)-7-hydroxy-2-quinolinone, the title compound was obtained as a white solid, m.p. 137°–138° C.

EXAMPLE 45

2-Cyano-4-phenyl-7-{3-[4-(4-methoxy)tetrahydropyranyl]benzyloxy}quinoline
Step 1: 7-tert-Butyldimethylsiloxy-4-phenyl-quinoline A mixture of 7-hydroxy-4-phenylquinoline (366 mg), tert-butyldimethylsilyl chloride (200 mg) and imidazole (282 mg) in DMF (2 mL) was stirred at r.t. for 17 hr and then diluted with 5% aq. NaHCO₃ (20 mL). The mixture was extracted with EtOAc (3×) and the combined organics were washed with H₂O (3×), brine, dried (MgSO₄) and concentrated. Flash chromatography of the residue (silica gel; EtOAc/hexane (15:85)) provided the title compound as a solid.

Step 2: 2-Cyano-7-hydroxy-4-phenylquinoline

A mixture of 7-tert-butyldimethylsiloxy-4-phenyl-quinoline (458 mg) and m-chloroperoxybenzoic acid (470 mg) in CHCl₃ (5 mL) was stirred at r.t. for 6 hr and then diluted with CHCl₃ (5 mL). This solution was washed with saturated aq. NaHCO₃ (3×), brine, dried (MgSO₄) and concentrated. The residue was dissolved in CH₂Cl₂ (3 mL) and trimethylsilyl cyanide (181 μL) was added and stirred at r.t. for 5 min. Dimethylcarbamyl chloride (125 μL) was added and, after 12 hr, 10% aq. K₂CO₃ (20 mL) was added and the resulting mixture stirred vigorously for 15 min. The aqueous phase was extracted with CH₂Cl₂ (2×) and the combined organics were washed with brine, dried (Na₂SO₄) and concentrated. The residue was dissolved in THF (4 mL) and tetrabutylammonium fluoride (1M in THF; 2.14 mL) was added at 0° C. After stirring at r.t. for 30 min., NH₄OAc buffer was added and the aqueous phase extracted with EtOAc (3×). The combined organics were washed with buffer (2×), brine, dried (MgSO₄) and concentrated. Trituration of the residual material with hexane/CHCl₃ (3:1) provided the title compound as a light yellow solid.

Step 3: 2-Cyano-4-phenyl-7-{3-[4-(4-methoxy)tetrahydropyranyl]benzyloxy}quinoline Following the procedure described in Example 1, Step 4, but substituting 2-cyano-7-hydroxy-4-phenylquinoline for 7-hydroxy-4-phenyl-2-quinolinone, the title compound was obtained as a foam.

¹H NMR (300 MHz, CDCl₃): δ1.96–2.12 (m, 4H), 2.99 (s, 3H), 3.81–3.93 (m, 4H), 5.26 (s, 2H), 7.35–7.60 (m, 12H), 7.88 (d, 1H).

EXAMPLE 46

[1S,5R]2-Cyano-4-phenyl-7-{6-[3-(3α-hydroxy-6,8-dioxabicyclo[3.2.1]octanyl)]pyridin-2-ylmethoxy}quinoline Following the procedures described in Example 23, but substituting 2-cyano-7-hydroxy-4-phenylquinoline for 1-benzyl-4-(3-furyl)-7-hydroxy-2-quinolinone the title compound was obtained as a white solid, m.p. 185°–187° C.

EXAMPLE 47

4-(3-Furyl)-7-{3-[4-(4-hydroxy)tetrahydropyranyl]benzyloxy}quinoline
Step 1: 4-(3-Furyl)-7-hydroxyquinoline Following the procedures described in Example 44, Steps 1 and 2, but substituting 4-(3-furyl)-7-methoxy-2-quinolinone for 7-methoxy-4-phenyl-2-quinolinone, the title compound was obtained as a solid.

Step 2: 4-(3-Furyl)-7-{3-[4-(4-hydroxy)tetrahydropyranyl]benzyloxy}quinoline

Following the procedure described in Example 2, Step 3, but substituting 4-(3-furyl)-7-hydroxyquinoline for 7-hydroxy-1-methyl-4-phenyl-2-quinolinone, the title compound was obtained as a solid.

¹H NMR (300 MHz, acetone-d₆): δ1.62 (br d, 2H), 2.10 (dt, 2H), 3.75 (br dd, 2H), 3.91 (dt, 2H), 5.31 (s, 2H), 6.88 (dd, 1H), 7.30–7.57 (m, 6H), 7.78 (m, 2H), 8.04 (dd, 1H) 8.13 (d, 1H), 8.77 (d, 1H).

EXAMPLE 48

4-(3-Furyl)-7-{3-[4-(4-methoxy)tetrahydropyranyl]benzyloxy}quinoline

Following the procedure described in Example 1, Step 4, but substituting 4-(3-furyl)-7-hydroxyquinoline for 7-hydroxy-4-phenyl-2-quinolinone, the title compound was obtained as a foam.

¹H NMR (300 MHz, acetone-d₆): δ1.92–1.99 (m, 4H), 2.94 (s, 3H), 3.69–3.81 (m, 4H), 5.34 (s, 2H), 6.88 (dd, 1H), 7.31–7.51 (m, 5H), 7.57 (d, 1H), 7.64 (s, 1H), 7.80 (t, 1H), 8.03 (dd, 1H), 8.13 (d, 1H), 8.78 (d, 1H).

EXAMPLE 49

4-(3-Thienyl)-7-{3-[4-(4-hydroxy)tetrahydropyranyl]benzyloxy}quinoline
Step 1: 7-Hydroxy-4-(3-thienyl)quinoline Following the procedure described in Example 44, Steps 1 and 2, but substituting 7-methoxy-4-(3-thienyl)-2-quinolinone for 7-methoxy-4-phenyl-2-quinolinone, the title compound was obtained as a solid.

Step 2: 4-(3-Thienyl)-7-{3-[4-(4-hydroxy)tetrahydropyranyl]benzyloxy}quinoline

Following the procedure described in Example 2, Step 3, but substituting 7-hydroxy-4-(3-thienyl)quinoline for 7-hydroxy-1-methyl-4-phenyl-2-quinolinone, the title compound was obtained as a solid.

$^1$H NMR (300 MHz, acetone-d$_6$): δ1.64 (dq, 2H), 2.11 (dt, 2H), 3.77 (m, 2H), 3.91 (m, 2H), 5.34 (s, 2H), 7.30–7.46 (m, 5H), 7.53 (dt, 1H), 7.59 (d, 1H), 7.72 (dd, 1H), 7.77 (m, 2H), 8.02 (d, 1H), 8.81 (d, 1H).

EXAMPLE 50

4-(3-Thienyl)-7-{3-[4-(4-methoxy)tetrahydropyranyl]-benzyloxy}quinoline

Following the procedure described in Example 1, Step 4, but substituting 7-hydroxy-4-(3-thienyl)quinoline for 7-hydroxy-4-phenyl-2-quinolinone, the title compound was obtained as a foam.

$^1$H NMR (300 MHz, acetone-d$_6$): 1.95–2.01 (m, 4H), 2.94 (s, 3H), 3.69–3.81 (m, 4H), 5.35 (s, 2H), 7.30–7.34 (m, 2H), 7.39–7.52 (m, 4H), 7.58 (d, 1H), 7.65 (m, 1H), 7.71 (dd, 1H), 7.75 (dd, 1H), 8.01 (d, 1H), 8.80 (d, 1H).

EXAMPLE 51

3-Carbomethoxy-1-phenyl-6-{3-[4-(4-methoxy)tetrahydropyranyl]benzyloxy}isoquinoline Step 1: 3-Carbomethoxy-6-methoxy-1-phenyl-3,4-dihydroisoquinoline To a solution of 3-hydroxyphenylalanine methyl ester (1 g) in CH$_2$Cl$_2$ (20 mL) at 0° C. was added triethylamine (2 mL) followed by DMAP (527 mg) and benzoyl chloride (1.1 mL). When addition was complete, the mixture was stirred for 17 hr at r.t. and then NH$_4$OAc buffer was added. The aqueous phase was extracted with CH$_2$Cl$_2$ (3×) and the combined organics were washed with buffer, brine, dried (MgSO$_4$) and concentrated. The residue was dissolved in MeOH (15 mL) and THF (1.5 mL) and NaOMe (1M in MeOH; 2.4 mL) was added at 0° C. After 2.5 hr, saturated aq. NH$_4$Cl was added and the aqueous phase extracted with EtOAc (3×). The combined organics were washed with NH$_4$OAc buffer (2×), H$_2$O, brine, dried (Na$_2$SO$_4$) and concentrated. Flash chromatography of the residue (silica gel; hexane/EtOAc (1:1)) provided N-benzoyl-3-hydroxyphenylalanine methyl ester as a foam. A portion of this material (1.25 g), K$_2$CO$_3$ (866 mg) and methyl iodide (312 μL) in DMF (12 mL) were stirred at r.t. for 18 hr and then H$_2$O (150 mL) was added. The mixture was extracted with EtOAc (3×) and the combined organics washed with NH$_4$OAc buffer, H$_2$O (2×) and brine, dried (MgSO$_4$) and concentrated. Flash chromatography of the residue (silica gel; hexane/EtOAc (55:45)) provided N-benzoyl-3-methoxyphenylalanine methyl ester as a gum. A portion of this material (950 mg) was dissolved in refluxing xylene (25 mL) and P$_2$O$_5$ (10.9 g) was added periodically over 5 hr. After refluxing for 5.5 hr, the mixture was cooled to r.t. and the xylene was decanted. The residual solid was dissolved in cold H$_2$O (600 mL) and neutralized with solid NaHCO$_3$. The aqueous mixture was extracted with EtOAc (3×) and the combined organics were washed with NH$_4$OAc buffer (2×), brine, dried (MgSO$_4$) and concentrated. Flash chromatography of the residue (silica gel; hexane/EtOAc (3:2)) provided the title compound as a gum.

Step 2: 3-Carbomethoxy-6-methoxy-1-phenylisoquinoline

A mixture of 3-carbomethoxy-6-methoxy-1-phenyl-3,4-dihydro-isoquinoline (257 mg) and DDQ (217 mg) in benzene (35 mL) was heated at reflux for 1 hr. the mixture was cooled to r.t., filtered through celite washing with toluene and the filtrate was concentrated. Flash chromatography of the residue (silica gel; toluene/EtOAc (85:15)) provided the title compound as a solid.

Step 3: 3-Carbomethoxy-6-hydroxy-1-phenylisoquinoline

A mixture of 3-carbomethoxy-6-methoxy-1-phenylisoquinoline (228 mg) and pyridine hydrochloride (700 mg) was heated at 170° C. for 6 hr. While still hot, H$_2$O (15 mL) was added and the precipitate that formed was collected. The aqueous phase was extracted with EtOAc (5×) and the combined organics were dried (Na$_2$SO$_4$) and concentrated. The residual material was combined with the precipitate and dissolved in MeOH (20 mL) and conc. HCl (10 drops). After refluxing for 60 hr, the mixture was cooled to r.t., NH$_4$OAc buffer was added and the mixture was extracted with EtOAc (3×). The combined organics were washed with buffer, brine, dried (MgSO$_4$) and concentrated. Trituration of the residue with hexane/EtOAc (9:1) provided the title compound as a solid.

Step 4: 3-Carbomethoxy-1-phenyl-6-{3-[4-(4-methoxy)-tetrahydropyranyl]benzyloxy}isoquinoline Following the procedure described in Example 1, Step 4, but substituting 3-carbomethoxy-6-hydroxy-1-phenylisoquinoline for 7-hydroxy-4-phenyl-2-quinolinone, the title compound was obtained as a solid, m.p. 126°–128° C.

EXAMPLE 52

3-Carbomethoxy-1-phenyl-6-{3-[4-(4-hydroxy)tetrahydropyranyl]benzyloxy}isoquinoline Following the procedure described in Example 2, Step 3, but substituting 3-carbomethoxy-6-hydroxy-1-phenylisoquinoline for 7-hydroxy-1-methyl-4-phenyl-2-quinolinone, the title compound was obtained as a white solid, m.p. 127°–130° C.

EXAMPLE 53

3-Carboxyl-1-phenyl-6-{3-[4-(4-methoxy)tetrahydropyranyl]benzyloxy}isoquinoline

To a solution of 3-carbomethoxy-1-phenyl-6-{3-[4-(4methoxy)tetrahydropyranyl]benzyloxy}isoquinoline (133 mg) in THF (6.5 mL) and MeOH (1.7 mL) was added LiOH (1N in H$_2$O; 550 μL). After stirring for 16 hr, NH$_4$OAc buffer was added and the mixture extracted with EtOAc (3×). The combined organics were washed with buffer (2×), brine, dried (Na$_2$SO$_4$) and concentrated to provide the title compound as a foam.

$^1$H NMR (300 MHz, CDCl$_3$): δ1.96–2.11 (m, 4H), 2.99 (s, 3H), 3.8–3.93 (m, 4H), 5.28 (s, 2H), 7.39–7.71 (m, 11H), 8.12 (d, 1H), 8.52 (s, 1H).

EXAMPLE 55 m.p. 137°–138° C.

EXAMPLE 56

$^1$H NMR (300 MHz, CDCl$_3$): δ1.91 (dd, 2H), 2.34 (d, 1H), 2.58 (dd, 1H), 3.81 (t, 1H), 4.56 (d, 1H), 4.68 (t, 1H), 5.06 (s, 1H), 5.10 (s, 2H), 5.49 (br s, 2H), 5.75 (s, 1H), 6.65 (s, 1H), 6.77–6.85 (m, 2H), 7.19–7.32 (m, 7H), 7.44–7.47 (m, 3H), 7.61–7.70 (m, 2H).

EXAMPLE 57

$^1$H NMR (300 MHz, CDCl$_3$): δ1.94 (dd, 2H), 2.36 (d, 1H), 2.60 (dd, 1H), 3.84 (t, 1H), 4.58 (d, 1H), 4.71 (t, 1H), 5.05 (s, 1H), 5.16 (s, 2H), 5.48 (br s, 2H), 5.78 (s, 1H), 6.67 (s, 1H), 6.81–6.84 (m, 2H), 6.96 (t, 2H), 7.21–7.29 (m, 4H), 7.45–7.50 (m, 3H), 7.65–7.72 (m, 2H).

EXAMPLE 58

$^1$H NMR (300 MHz, CDCl$_3$): δ1.93 (dd, 2H), 2.37 (d, 1H), 2.60 (dd, 1H, 3.83 (t, 1H), 4.58 (d, 1H), 4.71 (t, 1H), 5.02 (s, 1H), 5.16 (s, 2H), 5.46 (br s, 2H), 5.77 (s, 1H) 6.66 (s, 2H), 6.77 (s, 1H), 6.85 (d, 1H), 7.14–7.17 (m, 2H), 7.23–7.27 (m, 3H), 7.49 (d, 1H), 7.58 (m, 1H), 7.67–7.79 (m, 3H).

EXAMPLE 59 m.p. 157°–158° C. (decomp.)

EXAMPLE 60 m.p. 150°–153° C.

EXAMPLE 61

$^1$H NMR (300 MHz, acetone-d$_6$): δ1.81–1.92 (m, 2H), 2.48–2.53 (m, 1H), 2.65 (dd, 1H), 3.67 (t, 1H), 4.54 (d, 1H), 4.64 (t, 1H), 4.72 (s, 1H), 5.50 (s, 2H), 5.63 (s, 1H), 7.01 (s, 1H), 7.52–7.59 (m, 2H), 7.70 (d, 1H), 7.82–7.89 (m, 3H), 8.11 (s, 1H), 8.16–8.23 (m, 3H), 8.30 (d, 1H).

EXAMPLE 62 m.p. 158°–159° C. (decomp.)

EXAMPLE 63

$^1$H NMR (300 MHz, acetone-d$_6$): δ1.81–1.92 (m, 2H), 2.46–2.52 (m, 1H), 2.66 (dd, 1H), 3.67 (t, 1H), 4.54 (d, 1H), 4.66 (t, 1H), 4.71 (s, 1H), 5.41 (s, 2H), 5.65 (s, 1H), 7.33–7.43 (m, 3H), 7.49 (d, 1H), 7.58 (d, 1H), 7.67–7.77 (m, 3H), 7.85 (t, 1H), 8.04 (d, 1H), 8.80 (d, 1H).

EXAMPLE 64

$^1$H NMR (300 MHz, acetone-d$_6$): δ1.95–2.05 (m, 2H), 2.18–2.23 (m, 1H), 2.36 (dd, 1H), 3.66 (t, 1H), 4.25 (s, 1H), 4.52 (d, 1H), 4.64 (t, 1H), 5.39 (s, 2H), 5.63 (s, 1H), 7.01 (s, 1H), 7.37–7.53 (m, 4H), 7.62 (d, 1H), 7.74 (s, 1H), 7.80 (s, 1H), 7.86 (d, 1H), 8.19 (s, 1H), 8.27 (d, 1H).

What is claimed is:

1. A compound of the Formula I:

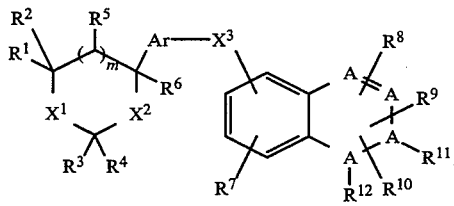

wherein:

$R^1$ is H, OH, lower alkyl, or lower alkoxy;
$R^2$ is H;
$R^3$ is H, lower alkyl, hydroxy lower alkyl, lower alkoxy lower alkyl, or is joined to $R^1$ to form a carbon bridge of 2 or 3 carbon atoms or a a mono-oxa carbon bridge of 1 or 2 carbon atoms, said bridge optionally containing a double bond;
$R^4$ is H;
$R^5$ is H;
$R^6$ is H, OH, lower alkyl, lower alkoxy, lower alkylthio or lower alkylcarbonyloxy;
$R^7$ and $R^{14}$ is each independently H, halogen, lower alkyl, hydroxy, lower alkoxy, CF$_3$, CN, COR$^{15}$, or C(R$^{15}$)$_2$OH;
$R^8$ is H, oxo, thioxo, halogen, CN, CF$_3$, lower alkoxy, or COR$^{13}$, with the proviso that when $R^8$ is H, $R^6$ is not OH;
$R^9$ is aryl($R^{14}$)$_2$ wherein aryl is Phe, Fu or Th;
$R^{10}$ is phenyl($R^{14}$)$_2$, phenyl($R^{14}$)$_2$-lower alkyl, naphthyl($R^{14}$)$_2$, naphthyl($R^{14}$)$_2$-lower alkyl, or c-Hex-lower alkyl;
$R^{11}$ and $R^{12}$ is each H or together form a bond;
$R^{13}$ is H or lower alkyl;
$R^{15}$ is H;
$X^1$ is O;
$X^2$ is C($R^{15}$)$_2$;
$X^3$ is C($R^{15}$)$_2$O;
Ar is phenylene or 6,2-Pye;
m is 1;
A is C or N with the proviso that one and only one A is N;
or a pharmaceutically acceptable salt thereof.

2. A compound of claim 1 of the Formula Ia:

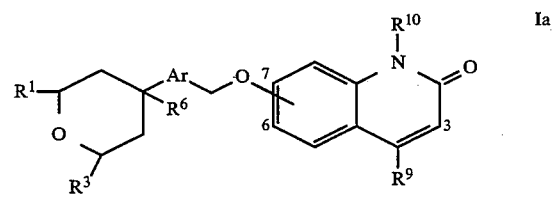

wherein:

$R^1$ and $R^3$ is each independently H or CH$_3$, or together are —CH$_2$CH$_2$—, CH$_2$O—, or —OCH$_2$—;
$R^6$ is OH or OMe;
$R^9$ is Ph, 3-Fu, or 3-Th;
$R^{10}$ is c-Hex-CH$_2$, Ph, PhCH$_2$ or naphthyl-CH$_2$;
Ar is 3-Phe, 5,3-Pye, 4,2-Pye, 2,4-Pye, 6,2-Pye, or 2,4-Tze; and
the ArCH$_2$O link is attached at position 6 or 7 of the quinolinone.

3. A compound of claim 1 of the Formula Ib:

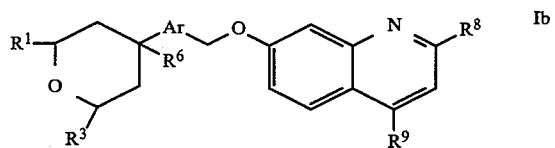

wherein:

$R^1$ and $R^3$ is each H or together are —CH$_2$O—;
$R^6$ is OH or OMe;
$R^8$ is H, OMe, or CN;
$R^9$ is Ph, 3-Fu, or 3-Th; and
Ar is 3-Phe or 6,2-Pye.

4. A compound of claim 1 of the Formula Id:

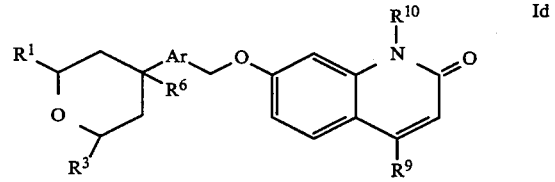

wherein the substituents are as follows:

| Ex. | $R^1$ | $R^3$ | $R^6$ | $R^9$ | $R^{10}$ | Ar |
|---|---|---|---|---|---|---|
| 5 | H | H | OH | Ph | PhCH$_2$ | 3-Phe |
| 6 | H | H | OMe | Ph | PhCH$_2$ | 3-Phe |
| 8 | H | H | OMe | Ph | 4-NCPheCH$_2$ | 3-Phe |
| 10 | H | H | OMe | Ph | c-HexCH$_2$ | 3-Phe |
| 11 | H | H | OMe | Ph | 1-C$_{10}$H$_7$CH$_2$** | 3-Phe |
| 13 | H | H | OMe | Ph | 3-MeO$_2$CPheCH$_2$ | 3-Phe |
| 14 | H | H | OMe | Ph | Ph | 3-Phe |
| 15 | H | H | OH | 3-Fu | PhCH$_2$ | 3-Phe |
| 16 | H | H | OMe | 3-Fu | PhCH$_2$ | 3-Phe |
| 17 | H | H | OMe | 3-Fu | 4-ClPheCH$_2$ | 3-Phe |
| 18 | —CH$_2$O— | | OH | 3-Fu | PhCH$_2$ | 3-Phe |
| 21 | H | H | OH | 3-Fu | 4-FPheCH$_2$ | 6,2-Pye |
| 22 | H | H | OH | 3-Fu | 4-ClPheCH$_2$ | 6,2-Pye |
| 23 | —CH$_2$O— | | OH | 3-Fu | PhCH$_2$ | 6,2-Pye |
| 24 | H | H | OH | 3-Th | PhCH$_2$ | 3-Phe |
| 25 | H | H | OMe | 3-Th | PhCH$_2$ | 3-Phe |
| 32 | H | H | OH | 3-Th | PhCH$_2$ | 6,2-Pye |
| 55 | —CH$_2$O— | | OH | 3-Fu | 4-FPheCH$_2$ | 6,2-Pye |
| 56 | —CH$_2$O— | | OH | 3-Th | PhCH$_2$ | 6,2-Pye |
| 57 | —CH$_2$O— | | OH | 3-Th | 4-FPheCH$_2$ | 6,2-Pye |
| 58 | —CH$_2$O— | | OH | 3-Fu | 4-ClPheCH$_2$ | 6,2-Pye |

**naphth-1-ylmethyl.

5. A compound of claim 1 of the Formula If:

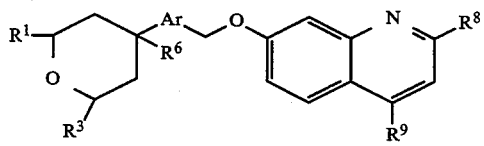

wherein the substituents are as follows:

| Ex. | $R^1$ | $R^3$ | $R^6$ | $R^8$ | $R^9$ | Ar |
|---|---|---|---|---|---|---|
| 41 | H | H | OMe | OMe | Ph | 3-Phe |
| 45 | H | H | OMe | CN | Ph | 3-Phe |
| 46 | —CH$_2$O— | | OH | CN | Ph | 6,2-Pye |
| 48 | H | H | OMe | H | 3-Fu | 3-Phe |

| Ex. | $R^1$ | $R^3$ | $R^6$ | $R^8$ | $R^9$ | Ar |
|---|---|---|---|---|---|---|
| 50 | H | H | OMe | H | 3-Th | 3-Phe |
| 59 | —CH$_2$O— | | OH | CN | 3-Fu | 6,2-Pye |
| 60 | —CH$_2$O— | | OH | CN | 3-Th | 6,2-Pye |
| 64 | —CH$_2$O— | | OH | CN | 3-Fu | 3-Phe. |

6. A compound of claim 1 of the Formula Ig:

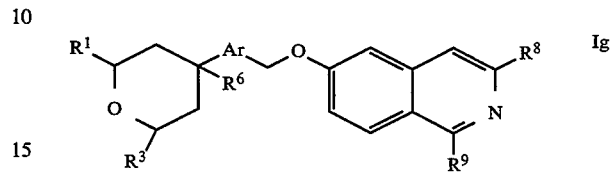

wherein the substituents are as follows:

| Ex. | $R^1$ | $R^3$ | $R^6$ | $R^8$ | $R^9$ | Ar |
|---|---|---|---|---|---|---|
| 67 | —CH$_2$O— | | OH | CN | 3-Fu | 6,2-Pye |
| 68 | —CH$_2$O— | | OH | CN | 3-Th | 6,2-Pye |
| 69 | —CH$_2$O— | | OH | CN | Ph | 6,2-Pye. |

7. A pharmaceutical composition comprising a therapeutically effective amount of a compound of claim 1 and a pharmaceutically acceptable carrier.

8. A method of preventing the action of leukotrienes in a mammal which comprises administering to said mammal an effective amount of a compound of claim 1.

9. The method of claim 8 wherein the mammal is man.

10. A method of treating asthma in a mammal comprising administering to a mammal in need of such treatment a therapeutically effective amount of a compound of claim 1.

11. A method of treating inflammatory diseases of the eye in mammal which comprises administering to a mammal in need of such treatment a therapeutically effective amount of a compound of claim 1.

* * * * *